US010077454B1

(12) United States Patent
Davis et al.

(10) Patent No.: US 10,077,454 B1
(45) Date of Patent: Sep. 18, 2018

(54) TANDEM BIOCHEMICAL AND THERMOCHEMICAL CONVERSION OF ALGAL BIOMASS

(71) Applicant: National Technology & Engineering Solutions of Sandia, LLC, Albuquerque, NM (US)

(72) Inventors: Ryan W. Davis, San Jose, CA (US); Anthe George, San Francisco, CA (US); Todd W. Lane, Livermore, CA (US); Ronald C. Pate, Corrales, NM (US); Benjamin C. Wu, San Ramon, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 52 days.

(21) Appl. No.: 14/750,960

(22) Filed: Jun. 25, 2015

Related U.S. Application Data

(60) Provisional application No. 62/017,118, filed on Jun. 25, 2014.

(51) Int. Cl.
C12P 7/06 (2006.01)
C12P 7/64 (2006.01)

(52) U.S. Cl.
CPC ............... C12P 7/065 (2013.01); C12P 7/649 (2013.01)

(58) Field of Classification Search
None
See application file for complete search history.

(56) References Cited

U.S. PATENT DOCUMENTS

| | | | |
|---|---|---|---|
| 6,030,587 A | 2/2000 | Haroldsen et al. | |
| 8,047,978 B1 | 11/2011 | Haroldsen et al. | |
| 8,481,974 B1 | 7/2013 | Davis et al. | |
| 8,969,056 B2 * | 3/2015 | Mody | C12P 7/06 435/161 |
| 9,034,595 B2 * | 5/2015 | Oldenburg | C12P 7/04 435/29 |
| 9,322,014 B1 | 4/2016 | VanderNoot et al. | |

OTHER PUBLICATIONS

Harun et al. Process Biochemistry. 2011, 46, 304-309.*
Ghareib et al. Folia Microbiol. 1988, 33, 447-452.*
U.S. Appl. No. 14/750,993, filed Jun. 25, 2015, Hewson et al.
U.S. Appl. No. 15/066,651, filed Mar. 10, 2016, Wu et al.
Behera S et al., "Scope of algae as third generation biofuels," *Front. Bioeng. Technol.* 2015;2:art. 90 (13 pp.).
Biddy M et al., "Whole algae hydrothermal liquefaction technology pathway," *National Renewable Energy Laboratory Technical Report NREL/TP-5100-58051*, Mar. 2013, 10 pp.
Davis RW et al., "Microaerobic fermentation of algae biomass for increased liquid fuels yield and nutrient recycling," *5th Congress of the International Society for Applied Phycology*, held on Jun. 23-27, 2014 in Sydney, Australia, presentation (16 pp.).
Davis RW et al., "Microaerobic fermentation of algae biomass residuals for fusel alcohol production and nutrient recycling," *3rd International Conference on Algal Biomass, Biofuels & Bioproducts*, held on Jun. 16-19, 2013 at Toronto, Canada, abstract (1 p).
Davis RW et al., "Microaerobic fermentation of algae biomass residuals for mixed alcohol production and nutrient recycling," *3rd International Conference on Algal Biomass, Biofuels & Bioproducts*, held on Jun. 16-19, 2013 at Toronto, Canada, presentation (12 p).
Davis RW et al., "Self-deconstructing algae biomass as feedstock for transportation fuels," Sandia Report No. SAND2014-17957, Sep. 2014 (43 pp.).
Demirbas A, "Use of algae as biofuel sources," *Energy Conversion Management* 2010;51:2738-49.
Dragone G et al., "Third generation biofuels from microalgae," in *Current research, technology and education topics in applied microbiology and microbial biotechnology*, A.M. Vilas (ed.), Formatex Research Center, Badajo, 2010, pp. 1355-1366.
Encarnação T et al., "Effect of N and P on the uptake of magnesium and iron and on the production of carotenoids and chlorophyll by the microalgae *Nannochloropsis* sp.," *J. Argi. Sci. Technol. A* 2012;2:824-32.
Geider R et al., "Redfield revisited: variability of C:N:P in marine microalgae and its biochemical basis," *Eur. J. Phycol.* 2002;37:1-17.
Hewson J et al., "Recovery of nutrients from biomass for nutrient recycling," *2013 Algae Biomass Summit*, held on Sep. 30-Oct. 3, 2013, Orlando, FL, presentation (23 pp.).
Huo YX et al., "Conversion of proteins into biofuels by engineering nitrogen flux," *Nat. Biotechnol.* 2011;29(4):346-51.
Huo YX et al., Supporting information for "Conversion of proteins into biofuels by engineering nitrogen flux," *Nat. Biotechnol.* 2011;29(4):346-51 (21 pp.).
Kofina AN et al., "Spontaneous precipitation of struvite from synthetic wastewater solutions," *Cryst. Growth Design* 2005;5(2):489-96.
Lane P et al., "Nutrient recycling for sustainable algal mass culture," *2013 Algae Biomass Summit*, held on Sep. 30-Oct. 3, 2013, Orlando, FL, presentation (17 pp.).
Lane P et al., "Nutrient recycling for sustained algal production," *2014 Algae Biomass Summit*, held on Sep. 29-Oct. 2, 2014, San Diego, CA, presentation (24 pp.).
Lane P et al., "Nutrient recycling for sustained algal production," *4th International Conference on Algal Biomass, Biofuels & Bioproducts*, held on Jun. 15-18, 2014, at Santa Fe, NM, presentation (26 pp.).
Lane TW et al., "Major nutrient recycling for sustainable algal mass culture," *5th International Conference on Algal Biomass, Biofuels & Bioproducts*, held on Jun. 7-10, 2015, at San Diego, CA, abstract (1 p.).

(Continued)

*Primary Examiner* — Vera Afremova
(74) *Attorney, Agent, or Firm* — Helen S. Baca

(57) ABSTRACT

The present invention relates to methods and system configured to convert algal biomass into biofuels, alcohols, nutrients, biochar, chemical building block compounds, and/or other useful by-products. Exemplary methods include an integrated biochemical and thermochemical process that provides high purity biofuels and mixed alcohols, while minimizing waste and/or maximizing efficiency.

25 Claims, 14 Drawing Sheets

(56) References Cited

OTHER PUBLICATIONS

Lane TW et al., "Major nutrient recycling for sustainable algal production," *4th International Conference on Algal Biomass, Biofuels & Bioproducts*, held on Jun. 15-18, 2014, at Santa Fe, NM, abstract (1 p.).

Lane TW et al., "Major nutrient recycling for sustained algal production," *DOE Bioenergy Technologies Office: 2015 Project Peer Review*, presented Mar. 25, 2015, presentation (28 pp.).

Liu X et al., "Pilot-scale data provide enhanced estimates of the life cycle energy and emissions profile of algae biofuels produced via hydrothermal liquefaction," *Bioresource Technol.* 2013;148:163-71.

Ma F et al., "Biodiesel production: a review," *Bioresource Technol.* 1999;70:1-15.

Naik SN et al., "Production of first and second generation biofuels: a comprehensive review," *Renew. Sustain. Energy Rev.* 2010;14:578-97.

Pate R et al., "Algal Turf to Fuel (ATF): production of biofuels from chemical, biochemical, and thermochemical processing and conversion of benthic polyculture biomass from algal turf systems," *4th International Conference on Algal Biomass, Biofuels & Bioproducts*, held on Jun. 15-18, 2014, at Santa Fe, NM, presentation (21 pp.).

Pate R et al., "Algal Turf to Fuel (ATF): system overview and preliminary assessment of the production of biofuels from chemical, biochemical, and thermochemical processing and conversion of benthic polyculture biomass produced by algal turf cultivation," *2014 Algae Biomass Summit*, held on Sep. 29-Oct. 2, 2014, San Diego, CA, presentation (26 pp.).

Pate R et al., "Resource demand implications for US algae biofuels production scale-up," *Appl. Energy* 2011;88:3377-88.

Raheem A et al., "Thermochemical conversion of microalgal biomass for biofuel production," *Renew. Sustain. Energy Rev.* 2015;49:990-9.

Rhodes C, "The Achilles' heel of algal biofuels: peak phosphate," *Forbes* Feb. 29, 2012 (2 pp.) (available at http://onforb.es/ybQiou, last accessed Jun. 26, 2015).

Ringer M et al., "Large-scale pyrolysis oil production: a technology assessment and economic analysis," *National Renewable Energy Laboratory Technical Report NREL/TP-510-37779*, Nov. 2006, 93 pp.

Schneider RCS et al., "Potential production of biofuel from microalgae biomass produced in wastewater," in *Biodiesel—Feedstocks, Production and Applications*, Prof. Zhen Fang (ed.), InTech, 2012, 22 pp.

Tran NH et al., "Catalytic upgrading of biorefinery oil from microalgae," *Fuels* 2010;89:265-74.

Wildschut J et al., "Catalyst studies on the hydrotreatment of fast pyrolysis oil," *Appl. Catalysis B* 2010;99:298-306.

Wu W et al., "Improved algal biofuel yield through bioconversion of proteins to mixed alcohols and sesquiterpenes," *Symposium on Biotechnology for Fuels and Chemicals*, held on Apr. 27-30, 2015 at San Diego, CA, abstract (1 p.).

Wu W et al., "Improved algal biofuel yield through bioconversion of proteins to mixed alcohols and sesquiterpenes," *Symposium on Biotechnology for Fuels and Chemicals*, held on Apr. 27-30, 2015 at San Diego, CA, poster (1 p.).

Wyatt NB et al., "Struvite precipitation as a path for algae nutrient recycling," *4th International Conference on Algal Biomass, Biofuels & Bioproducts*, held on Jun. 15-18, 2014, at Santa Fe, NM, abstract (1 p.).

Wyatt NB et al., "Struvite precipitation as a path for algae nutrient recycling," *4th International Conference on Algal Biomass, Biofuels & Bioproducts*, held on Jun. 15-18, 2014, at Santa Fe, NM, presentation (23 pp.).

Xin L et al., "Effects of different nitrogen and phosphorus concentrations on the growth, nutrient uptake, and lipid accumulation of a freshwater microalga *Scenedesmus* sp.," *Bioresource Technol.* 2010;101:5494-500.

Yue D et al., "Biomass-to-bioenergy and biofuel supply chain optimization: overview, key issues and challenges," *Computers Chem. Eng.* 2014;66:36-56.

\* cited by examiner

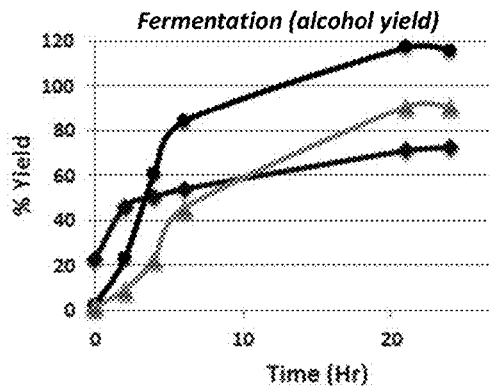
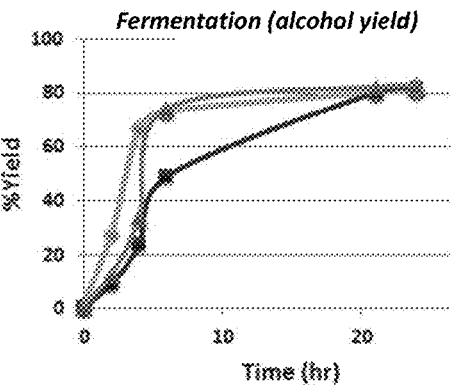
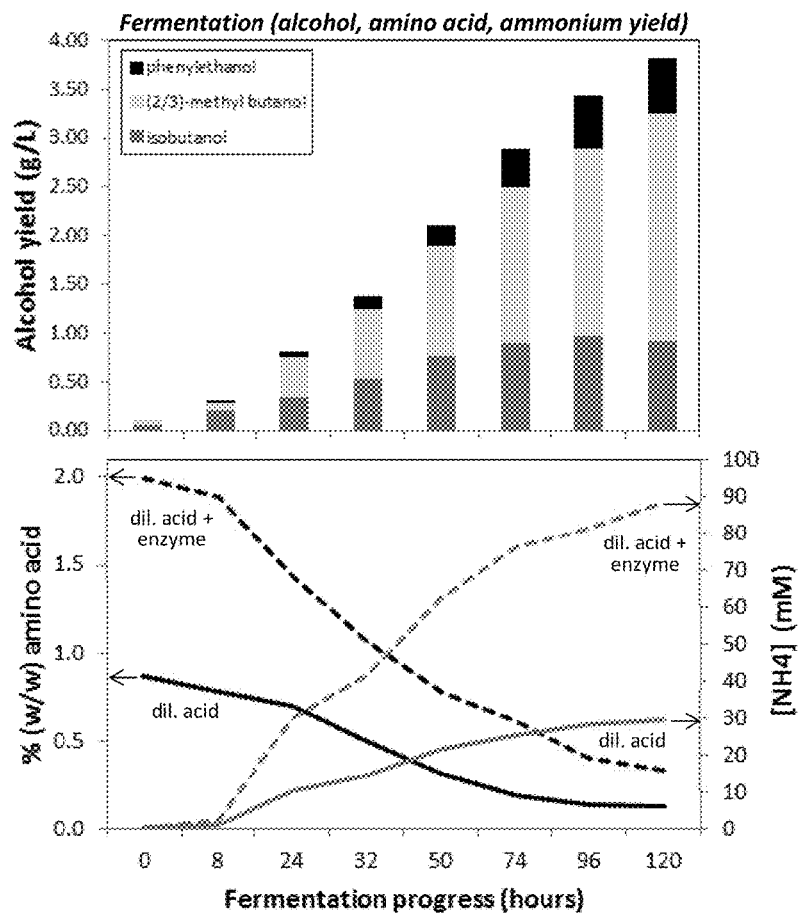
FIG. 7A
FIG. 7B
FIG. 7C

TANDEM BIOCHEMICAL AND THERMOCHEMICAL CONVERSION OF ALGAL BIOMASS

CROSS-REFERENCE TO RELATED APPLICATION

This application claims the benefit of U.S. Provisional Application No. 62/017,118, filed Jun. 25, 2014, which is hereby incorporated by reference in its entirety.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to methods and system configured to convert algal biomass into biofuels, alcohols, and/or other useful by-products. Exemplary methods include an integrated biochemical and thermochemical process that provides high purity biofuels and mixed alcohols, while minimizing waste and/or maximizing efficiency. Furthermore, the process can be further configured to provide useful by-products, such as chemical building block compounds, biochar, and/or nutrients.

BACKGROUND OF THE INVENTION

Algae have useful industrial purposes, such as for use as a biofuel crop or for waste water treatment. In particular, algae have the potential to provide a renewable supply for liquid fuels. Recent work for algae biofuel development has primarily focused on production of high lipid algae; however, this goal has not been achieved in high productivity within outdoor cultures. Furthermore, processing of algal biomass can be energy-intensive, which in turn can lead to an expensive industrial process flow in order to obtain pure, low nitrogen bio-oils. Accordingly, there is a need for new systems and methods that provide low cost, high efficiency production of biofuels from algal biomass sources.

SUMMARY OF THE INVENTION

The present invention relates to methods and systems configured to convert algal biomass into useful products, including biocrude oils, alcohols including bioethanol, and/or biofuels. In particular embodiments, the methods and systems herein employ a consolidated process that includes use of all viable biocomponents derived from an algal biomass. As compared to other methods, drying of the biomass is not required. Rather, a wet algal biomass can be harvested and employed without further drying, thereby saving energy that is typically expended for drying algal biomass.

Fermenting of one or more biocomponents, such as proteins and carbohydrates derived from the algal biomass, can provide useful by-products, including mixed alcohols, amino acids, amines (e.g., primary, secondary, and tertiary amines, as well as ammonium forms thereof), and liberated nutrients (e.g., minerals, elements such as nitrogen or phosphorous, etc.). However, the progress of the fermentation reaction can be limited by the formation of inhibitory by-products during the fermentation process. Thus, in some embodiments, we conducted the fermentation reaction in the presence of both aqueous-soluble biocomponents (e.g., proteins and/or carbohydrates) and aqueous-insoluble biocomponents (e.g., lipids). In this way, the fermentation reaction is conducted in the presence of these two phases (i.e., aqueous-soluble and aqueous-insoluble phases), which reduces product inhibition by phase segregation of inhibitory products into one of the two phases.

Furthermore, the presence of some types of lipids (e.g., triacylglycerides) enhanced the fermentation reaction. As most organisms used for fermentation are sensitive to alcohol within the fermentation broth, alcohol toxicity can be reduced by using this two-phase system (e.g., by partitioning of the alcohol products within a micelle or vesicle formed with one or more lipids, thereby spatially separating viable yeast and/or bacteria from potentially harmful concentrations of alcohol). In this way, the fermentation step reflects a consolidated bioprocessing step by including both the lipid and protein biocomponents within the fermentation broth.

Accordingly, in a first aspect, the present invention features a method of converting algal biomass, the method including: pre-treating the algal biomass with one or more acids and/or one or more enzymes, thereby providing a combination of ash and one or more biocomponents; fermenting the one or more biocomponents, thereby providing one or more fermentation products and a bioresidue including one or more lipid products; separating the one or more fermentation products from the bioresidue; and liquefying and/or pyrolyzing the bioresidue. In one instance, the method thereby provides a biocrude oil and/or a biogas.

In some embodiments, the pre-treating step includes i) treating the algal biomass with one or more acids (e.g., a dilute acid) and ii) treating with one or more enzymes (e.g., one or more proteases), where the steps i) and ii) can be conducted sequentially in any order or at the same time. In other embodiments, the method further includes, after the pre-treating step, separating the ash from the combination.

In some embodiments, the fermenting step includes exposing the one or more biocomponents to one or more organisms (e.g., bacteria and/or yeast) or mutant forms thereof.

In other embodiments, the fermenting step is conducted in the presence of the one or more biocomponents including at least one protein, at least one carbohydrate, and at least one lipid derived from the algal biomass, thereby promoting the formation of one or more lipid microparticles.

In some embodiments, the fermenting step includes use of an aerobic and/or an anaerobic condition. In other embodiments, the fermenting step includes initial use of an aerobic condition for a first time period (e.g., of from about 0 to 24 hours after beginning fermentation) and then latter use of an anaerobic condition for a second time period (e.g., of from about 18 to 72 hours after beginning fermentation).

In some embodiments, the fermenting step includes removing one or more by-product nutrients present in a same phase as the one or more fermentation products.

In some embodiments, the one or more lipid products include one or more lipids derived from the algal biomass (e.g., one or more triglycerides and one or more fatty acids).

In some embodiments, the one or more fermentation products are present in a first phase (e.g., an aqueous phase) and the bioresidue is present in a second phase (e.g., a non-aqueous phase or a lipid phase) that is separate from the first phase.

In some embodiments, the separating step is conducted by extracting the bioresidue with one or more lipophilic solvents or solvent mixtures (e.g., solvents such as hexane, benzene, dichloromethane, as well as mixtures thereof).

In some embodiments, after the separating step, the method includes processing the one or more fermentation products to provide one or more alcohols (e.g., selected from the group of ethanol, propanol, butanol, and alkylated formed thereof).

In some embodiments, the liquefying step includes exposing the bioresidue to a non-catalytic or catalytic condition including a temperature of from about 200° C. to about 500° C. In some embodiments, the liquefying step is conducted in the presence of an aqueous solvent (e.g., water, such as that present in a wet algal biomass). In other embodiments, the liquefying step is conducted under a pressure of from about 0.5 to about 20 MPa. In yet other embodiments, the liquefying step further provides a biochar. In further embodiments, the method include, after the liquefying step, separating the biocrude oil from the biochar.

In some embodiments, the liquefying step further provides an aqueous phase including one or more nutrients. In further embodiments, the method includes, after the liquefying step, separating the biocrude oil from the aqueous phase; and capturing the one or more nutrients (e.g., nitrogen, phosphorus, etc.) present in the aqueous phase. In other embodiments, the method includes, after the liquefying step, converting the biocrude oil into one or more biofuels (e.g., biodiesel, hydrocarbons, or any other biofuel described herein).

In a second aspect, the present invention features a method of converting algal biomass, the method including: pre-treating the algal biomass with one or more acids and/or one or more enzymes, thereby providing a combination of ash and one or more biocomponents; separating the one or more biocomponents to provide a first fraction including one or more soluble proteins and/or carbohydrates and a second fraction including a bioresidue including one or more lipids; fermenting the first fraction, thereby providing one or more fermentation products; and liquefying and/or pyrolyzing the bioresidue, thereby providing a biocrude oil. The fermenting and liquefying/pyrolyzing steps can be conducted in any order or at the same time.

In some embodiments, the liquefying step further includes providing an aqueous phase. In other embodiments, the method further includes, after the liquefying step, capturing one or more nutrients present in the aqueous phase.

In a third aspect, the present invention features a method of converting algal biomass, the method including: pre-treating the algal biomass with one or more acids and/or one or more enzymes, thereby providing a combination of ash and one or more biocomponents; separating the ash from the combination; fermenting the one or more biocomponents, thereby providing one or more fermentation products and a bioresidue including one or more lipid products; separating the one or more fermentation products from the bioresidue; liquefying and/or pyrolyzing the bioresidue, thereby providing a biocrude oil and an aqueous phase; and capturing one or more nutrients present in the aqueous phase.

In a fourth aspect, the present invention features a processing system configured to convert algal biomass (e.g., according to any method described herein). In one embodiment, the processing system includes a pre-treatment chamber configured to pre-treat the algal biomass with one or more acids and/or one or more enzymes, thereby providing a combination of ash and one or more biocomponents; a fermentation tank configured to ferment the one or more biocomponents, thereby providing one or more fermentation products and a bioresidue including one or more lipid products, where the fermentation tank is in fluidic communication with the pre-treatment chamber; a separator configured to separate the one or more fermentation products from the bioresidue, where the separator is in fluidic communication with the fermentation tank; and a thermal conversion chamber configured to liquefy and/or pyrolyze the bioresidue, wherein the thermal conversion chamber is in fluidic communication with the separator. In one instance, the method thereby provides a biocrude oil and/or a biogas.

In any embodiment herein, the algal biomass includes a wet algal biomass, a dry algal biomass, a monoculture biomass, and/or a polyculture biomass. In some embodiments, the algal biomass includes one or more microalgae, macroalgae, diatoms, green algae, yellow algae, phytoplankton, haptophytes, protists, and/or cyanobacteria (e.g., any described herein).

In any embodiment herein, the one or more biocomponents include one or more proteins, carbohydrates, and/or lipids derived from the algal biomass.

In any embodiment herein, the biocrude oil has a low nitrogen content.

In any embodiment herein, the pre-treating step includes treating the algal biomass with one or more acids (e.g., a dilute acid) and/or treating with one or more enzymes (e.g., one or more proteases).

In any embodiment herein, the fermenting step is conducted in the presence of at least one lipid, lipid particle, or lipid vesicle derived from the algal biomass, thereby promoting the formation of one or more lipid microparticles.

In any embodiment herein, the fermenting step includes use of an aerobic and/or an anaerobic condition.

Definitions

As used herein, the term "about" means+/−10% of any recited value. As used herein, this term modifies any recited value, range of values, or endpoints of one or more ranges.

Other features and advantages of the invention will be apparent from the following description and the claims.

BRIEF DESCRIPTION OF THE DRAWINGS

FIG. 7A-7C shows the effect of fermentation conditions on pre-treated algal biomass. Provided are (A) ethanol yield for a *Chlorella* biomass sample; (B) ethanol yield for a *Scenedesmus* biomass sample; and (C) alcohol, amino acid, and ammonium ($NH_4$) yield for a pre-treated algal biomass sample employing a sugar fermentation strain (*Zymomonas* sp. bacteria) for converting C5 and C6 sugars and a protein fermentation strain (*E. coli* YH83 bacteria) for converting amino acids to >C2 alcohols and $NH_4$. Samples were pre-treated with dilute acid alone or with a combination of a dilute acid with enzyme treatment. About 70% of theoretical protein conversion was achieved with bench scale testing.

DETAILED DESCRIPTION OF THE INVENTION

The present invention relates to the conversion of algal biomass (e.g., wet algal biomass) I into fuel intermediates, such as bioresidue, biocrude oil, etc. Such fuel intermediates, in turn, can be suitable for downstream refining, e.g., using known petrochemical facilities and processes. In particular embodiments, an exemplary process of the invention combines wet pre-treatment of the algal biomass to solubilize and hydrolyze the carbohydrate and protein fractions; followed by fermentation, lipid and alcohol co-extraction, nutrient capture, and hydrothermal liquefaction of the residuals. In some embodiments, the process employs both biochemical and thermochemical steps to effectively solubilize, hydrolyze, and/or degrade components of the biomass.

Figure 1A:
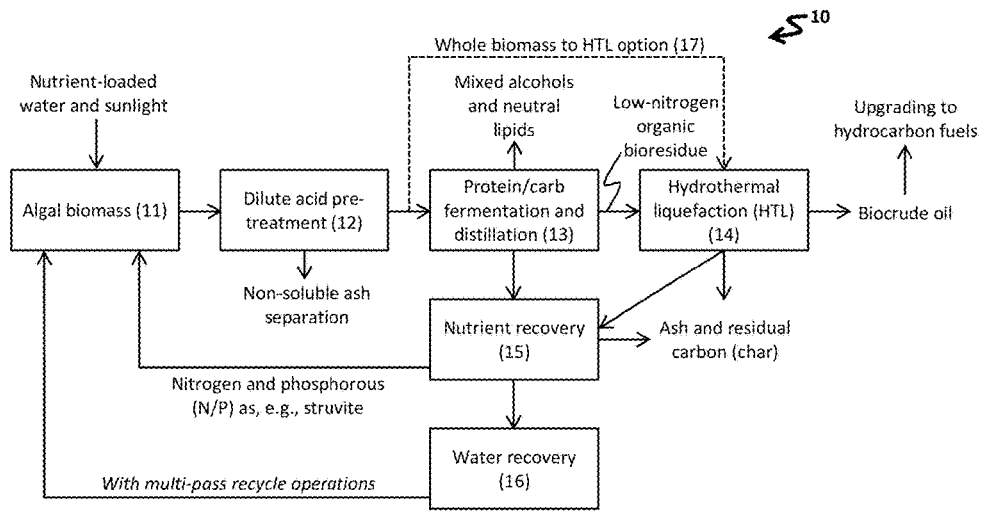
FIG. 1A-1D shows exemplary process flow diagrams for tandem biochemical and thermochemical processing of algal biomass. Provided are (A) an exemplary process 10 including processing and recycling pathways and (B) another exemplary process 20 including additional harvesting and distilling pathways. The unit operations of the process are depicted as designated boxes, where inputs and outputs for life cycle assessment and technoeconomic analysis are designated by arrows leading either into or away from a box. Also provided are (C) an exemplary process 100 with various steps; and (D) an exemplary process 1000 with inputs and outputs designated by gray arrows and gray boxes.

An exemplary integrated process 10 is shown in FIG. 1A. An algal biomass 11 is incubated with nutrient-loaded water and sunlight to promote growth, and then harvested. Typically, an algal biomass will include equal fractions of proteins, carbohydrates, and lipids (collectively, biocomponents). Further treatment steps can be employed to breakdown these biocomponents of the algal biomass into useful residuals. Exemplary steps include dilute acid pre-treatment 12 (optionally including a prior, subsequent, or simultaneous use of one or more enzymes) to hydrolyze and solubilize the biocomponents; as well as fermentation and distillation 13 to degrade the biocomponents into one or more alcohols, amino acids, and amines.

In some situations, pre-treatment will result in solubilization of useful biocomponents, as well as precipitation or separation of non-soluble components, such as ash. In particular, ash can be removed after this pre-treatment step to more effectively conduct downstream processing steps.

Fermentation is typically employed to degrade sugars, carbohydrates, and proteins into further, smaller chemical components, such as alcohols, amino acids, and amines. In use, fermentation employs one or more organisms, such as bacteria or yeast, to degrade these biocomponents. Typically, such organisms do not degrade lipids. Thus, conventional fermentation is usually conducted in aqueous, non-lipid samples. In some embodiments of the invention herein, organisms can be genetically modified to convert lipids. We have unexpectedly discovered that use of lipids during fermentation improves conversion yield of alcohols. Without wishing to be limited by mechanism, we believe that the presence of lipids results in the formation of lipid vesicles or micelles, which compartmentalize fermentation inhibitory products and further propagate the fermentation reaction. Thus, in other embodiments of the invention herein, the fermentation step includes use of one or more lipids, lipid vesicles, and/or lipid micelles within the fermentation broth.

In other examples, after the fermentation step, the aqueous and non-aqueous (e.g., lipid) fractions are phase-separated and processed in parallel steps. For instance, the non-aqueous fraction, including a bioresidue (e.g., a low nitrogen organic residue) composed of one or more lipids, will be treated by way of hydrothermal liquefaction (HTL) 14 to provide a biocrude oil. Any solid residuals, such as ash or char, can be removed after liquefaction. Any liquid residuals can be further processed to recover 15 any useful nutrients. Then, the aqueous fraction (e.g., including water-soluble components) can be distilled to remove alcohols (e.g., along with neutral lipids) and then further processed to recover any useful nutrients 15 (e.g., for recovering nitrogen and/or phosphorus) or usable water 16 (e.g., for use in multi-pass recycle operations) in the aqueous phase, as well as to extract any lipids present in the aqueous phase.

In other situations, the pre-treated biomass is not fermented and distilled. Rather, the whole biomass is directly treated 17 with hydrothermal liquefaction. Whole biomass treatment can provide a higher yield of the biocrude oil by avoiding intervening separating, extracting, or distilling steps. Nonetheless, in most situations, this will result in a higher-nitrogen content biocrude oil, which may require further purification step(s) to remove excess nitrogen in the oil.

Any useful thermochemical process can be employed to process a bioresidue into a biocrude oil. Exemplary thermochemical processes include liquefaction, pyrolysis, gasification, and/or combustion in the optional presence of one or more catalysts. Experimental conditions (e.g., temperature, pressure, air composition, reactants, reagents, etc.) can be optimized in any useful manner to achieve the desired biocrude oil with appropriate viscosity, color, oxygen content, nitrogen content, etc. In addition, the biocrude oil can be further upgraded into biofuels, such as by use of hydrotreatment (e.g., as described herein).

Figure 1B:
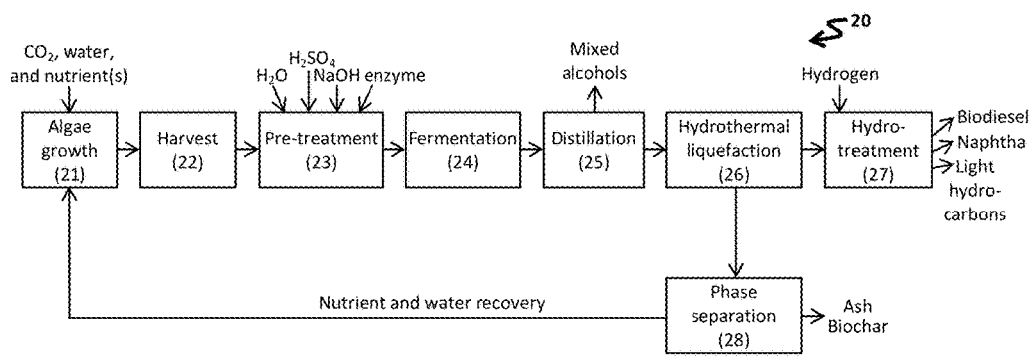

Another exemplary conversion process 20 is shown in FIG. 1B, which provides various inputs and outputs during the process. As can be seen, the process 20 includes a first step of algae growth 21, which is promoted by various inputs for $CO_2$, nutrients, vitamins, sunlight, and water. A subsequent harvest step 22 provides a wet algal biomass, which can then be pre-treated 23. This pre-treatment step 23 generally includes the most extensive use of inputs, including water, one or more acids (e.g., dilute or strong $H_2SO_4$), a neutralizer (e.g., a base, such as NaOH), and one or more enzymes (e.g., a protease or a protease cocktail). The fermentation step 24 results in conversion of the biocomponents (separated from the algal biomass through pre-treatment) into one or more smaller or simpler components, such as amino acids, keto acids, alcohols, amines, etc. Such smaller or simpler components can be further purified (e.g., extracted, distilled, precipitated, etc.) to provide pharmaceutical intermediates, chemicals, chemical/biochemical precursors, building blocks, reagents, and/or intermediates.

The distillation step 25 results in the separation of volatile fraction(s) from the less volatile fraction(s), resulting in, e.g., a fraction including mixed alcohols and another fraction including a predominantly non-aqueous, lipid phase (e.g., a bioresidue). The fraction including mixed alcohols can be further purified to provide bioethanol.

Then, the bioresidue can be thermally treated at a temperature sufficient to separate volatile lipids from solid residuals, such as by way of hydrothermal liquefaction 26, to produce a liquefied mixture. This liquefied mixture can include biocrude oil, ash, biochar, and other components. The biocrude oil, in turn, can be further processed, e.g., by way of hydrotreatment 27 with an input of hydrogen, to produce any useful biofuel, such as biodiesel, naphtha, or light hydrocarbons. Other components from the liquefied mixture can be phase separated 28 to extract the solid residuals, such as ash or biochar, from the liquid phase. This liquid phase can be further processed for nutrient and water recovery. Additional details of the process, as well as related steps, follow.

Methods of Converting Algal Biomass

The present invention relates to conversion of algal biomass into useful fuel intermediates, biofuels, or other chemical/biochemical precursors, intermediates, or reagents. Any useful method can be employed, particular those that employ pre-treatment, fermentation, and liquefaction steps to degrade useful protein-, carbohydrate-, and lipid-based biocomponents into biofuel and intermediates thereof. In particular embodiments, the method employs a consolidated fermentation step that includes all three protein-, carbohydrate-, and lipid-based biocomponents derived from the algal source.

Figure 1C:
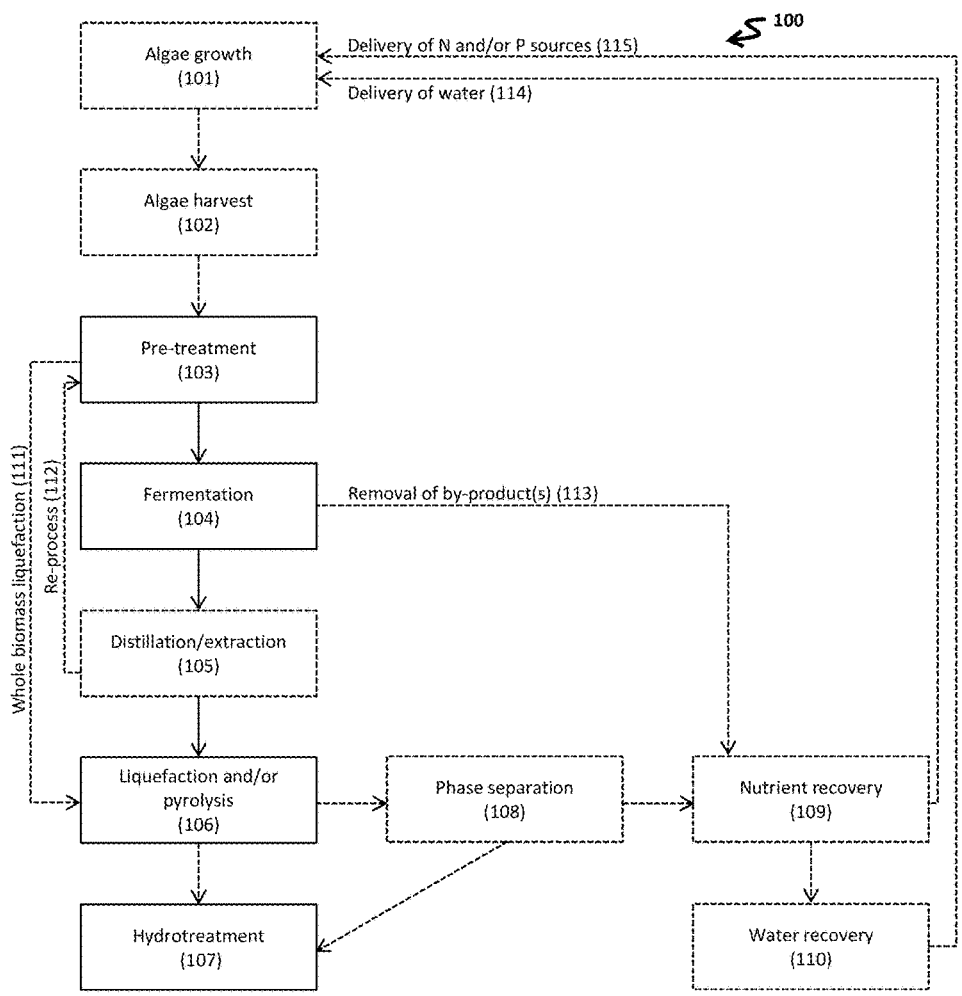

FIG. 1C shows an exemplary method 100 including optional steps of algae growth 101 and harvest 102. These steps are optional because, alternatively, the algal biomass can be provided or purchased for processing. The method 100 includes a pre-treatment step 103 of the algal biomass (e.g., as described herein) to provide biocomponents released from the pre-treated sample, followed by a fermentation step 104 and an optional distillation/extraction step 105. As needed, the algal biomass can be re-processed 112 to further hydrolyze, solubilize, and/or degrade the sample. After fermentation, one or more by-products (e.g., minerals, nutrients, water, etc.) can be optionally removed 113 from any of the fractions.

The liquefaction and/or pyrolysis step 106 can be performed on either the whole biomass 111 or on the pre-treated and fermented biomass. The resultant liquefied/pyrolyzed mixture can be directly subject to hydrotreatment 107 or to optional phase separation 108 with later hydrotreatment 107.

The present method also provides a streamlined procedure for recovering by-products 113, nutrients 109, and/or water 110 from any of the fractions or mixtures obtained during the conversion process. Any recovered, useful compounds can be delivered 114,115 back to algal culture tanks to promote algae growth 101.

Figure 1D:
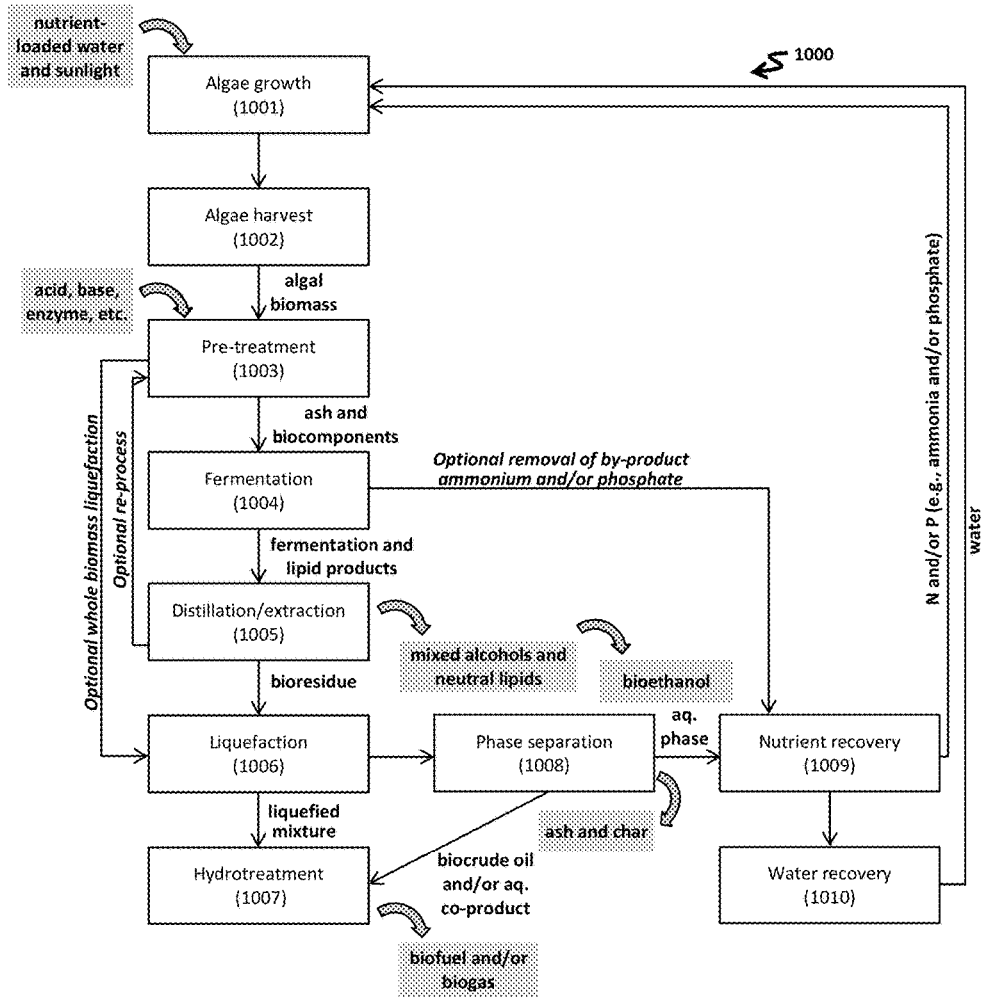

FIG. 1D provides additional detail on inputs and outputs related to an exemplary method 1000 of the invention including the steps of algae growth 1001, algae harvest 1002, pre-treatment 1003, fermentation 1004, distillation/extraction 1005, liquefaction/pyrolysis 1006, hydrotreatment 1007, phase separation 1008, nutrient recovery 1009, and water recovery 1010.

During algal growth 1001, nutrients, water, and sunlight are delivered to the algae. During pre-treatment 1003, acid, base, enzyme(s), etc. are delivered to the algal biomass, which in turn results in an output of ash and biocomponents released from the algal biomass. The biocomponents include hydrolyzed and/or solubilized cellular components derived from the algae, such as proteins, carbohydrates, and lipids. After fermentation 1004, the biocomponents are converted into a mixture of fermentation products and lipid products. After distillation and/or extraction 1005, the more volatile fraction can be extracted to include mixed lipids and neutral lipids, which in turn can be refined into bioethanol. The less volatile fraction can also be extracted, where this fraction will generally include lipid-like components and products designated a bioresidue. During liquefaction 1006, the bioresidue or whole biomass is employed as an input, which produces an output of a liquefied mixture.

During phase separation 1008, the liquefied mixture is employed as an input, which produces an output of an aqueous phase fraction, a liquid biocrude oil, and/or a solid residual, such as ash and char. During hydrotreatment 1007, either the liquefied mixture and/or the biocrude oil can be employed as input(s), which produce output(s) of a biofuel and/or a biogas. During nutrient recovery 1009, the input can be a fraction from the fermentation broth and/or an aqueous phase fraction from the liquefied mixture, which produces an output of nitrogen (e.g., as an ammonia) and/or phosphorous (e.g., as a phosphate).

Figure 2A:
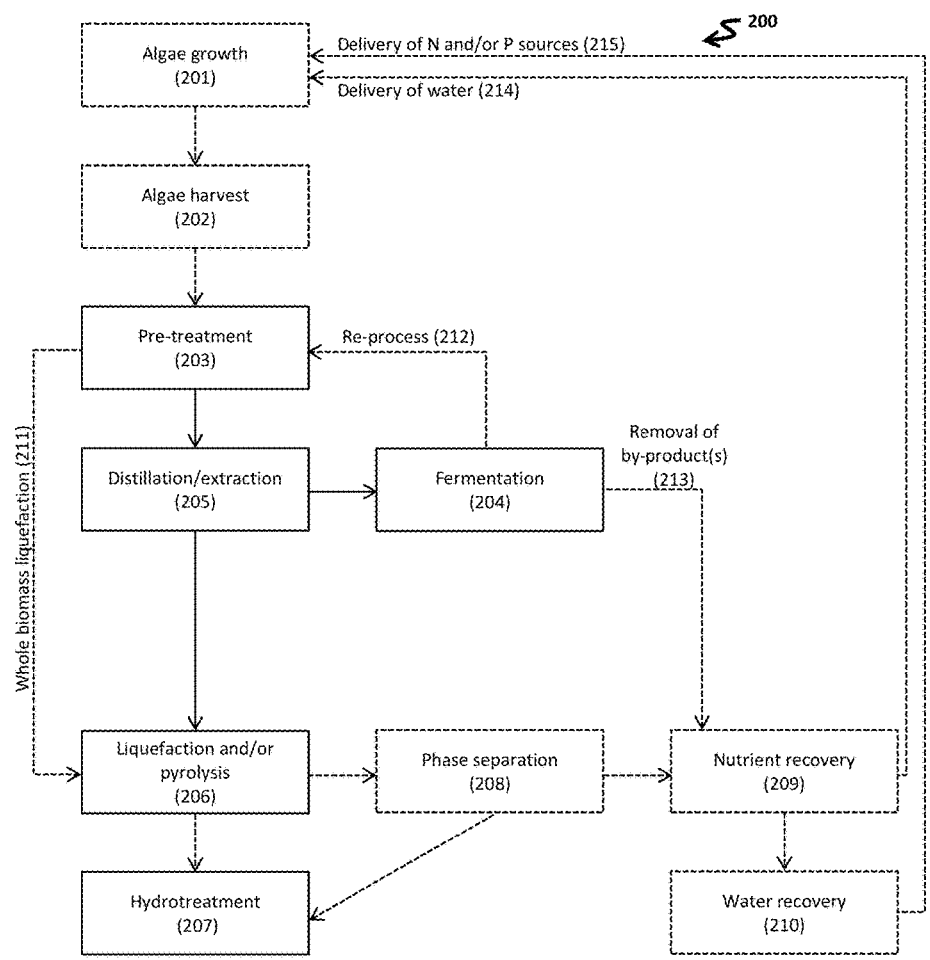
FIG. 2A-2B shows other exemplary process flow diagrams for tandem biochemical and thermochemical processing of algal biomass. Provided are (A) an exemplary process 200 in which fermentation 204 and liquefaction and/or pyrolysis 206 steps are conducted in parallel; and (B) an exemplary process 2000 with inputs and outputs designated by gray arrows and gray boxes.

In another example, the distillation/extraction and fermentation steps are performed in parallel. FIG. 2A provides an exemplary method 200 of the invention including the steps of optional algae growth 201, optional algae harvest 202, pre-treatment 203, distillation/extraction 205, fermentation 204, liquefaction and/or pyrolysis 206, hydrotreatment 207, optional phase separation 208, optional nutrient recovery 209, and optional water recovery 210. In one embodiment, the method 200 includes whole biomass liquefaction 211, in which a pre-treated biomass sample including biocomponents is directly liquefied or pyrolyzed. In another embodiment, the method 200 includes re-processing 212, in which pre-treatment 203, distillation/extraction 205, and fermentation 204 steps are repeated as needed.

Nutrients, by-products, and water can be extracted within any point of the processing stream and with any useful mixture obtained within the processing stream. Such extraction steps can include removal of by-products 213 from the fermentation broth or a portion thereof, delivery of nitrogen (N) and/or phosphorous (P) sources 215 (e.g., as a salt, a mineral, etc.), and/or delivery of water 214.

Figure 2B:
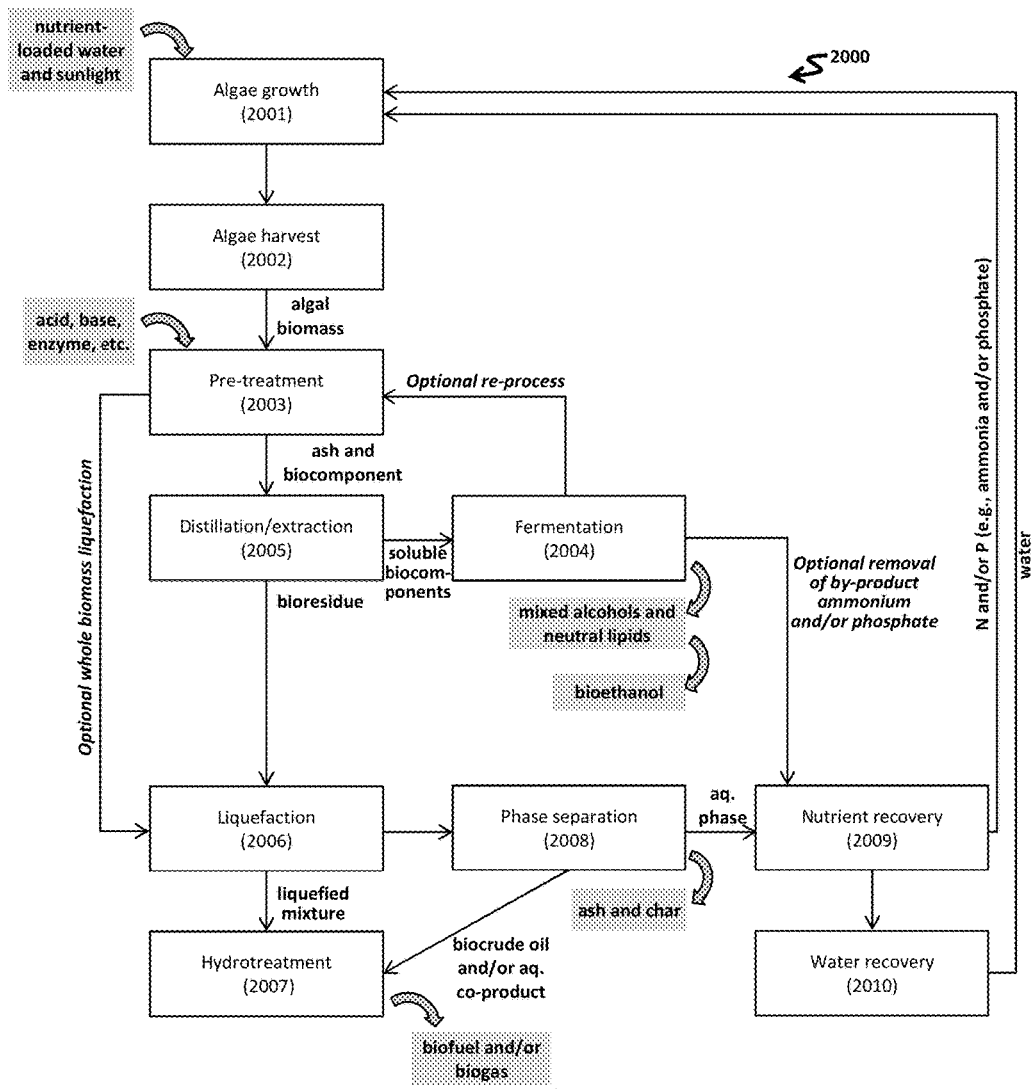

FIG. 2B provides additional detail on inputs and outputs related to an exemplary method 2000 of the invention including the steps of algae growth 2001, algae harvest 2002, pre-treatment 2003, distillation/extraction 2005, fermentation 2004, liquefaction 2006, hydrotreatment 2007, phase separation 2008, nutrient recovery 2009, and water recovery 2010. Inputs include nutrients, water, and sunlight that are delivered to the algae during algae growth 2001; as well as acid, base, enzyme, etc. that are delivered to the algal biomass during pre-treatment 2003. Outputs include an algal biomass after algae harvest 2002; ash and biocomponents after pre-treatment 2003; a volatile mixture (e.g., including one or more alcohols and other elutes, such as neutral lipids) obtained after fermentation 2004; a bioresidue and soluble biocomponents after distillation/extraction 2005; a liquefied mixture after liquefaction 2006; a biocrude oil, an aqueous phase, aqueous co-product(s), ash, and/or biochar after phase separation 2008; and biofuel and/or biogas after hydrotreatment 2007.

Single Pass and Multi-Pass Operations

The methods and systems herein can be employed in a single-pass operation and/or a multi-pass recycle operation. For instance, the methods herein can be characterized as a single-pass operation to convert algal biomass into desired biofuel and intermediates. In another instance, the methods herein can be characterized as a multi-pass recycle operation in which nutrients and by-products are recovered from processed biomass, and these recovered compounds are then recycled for any useful purpose, e.g., algae growth.

Figure 3A:
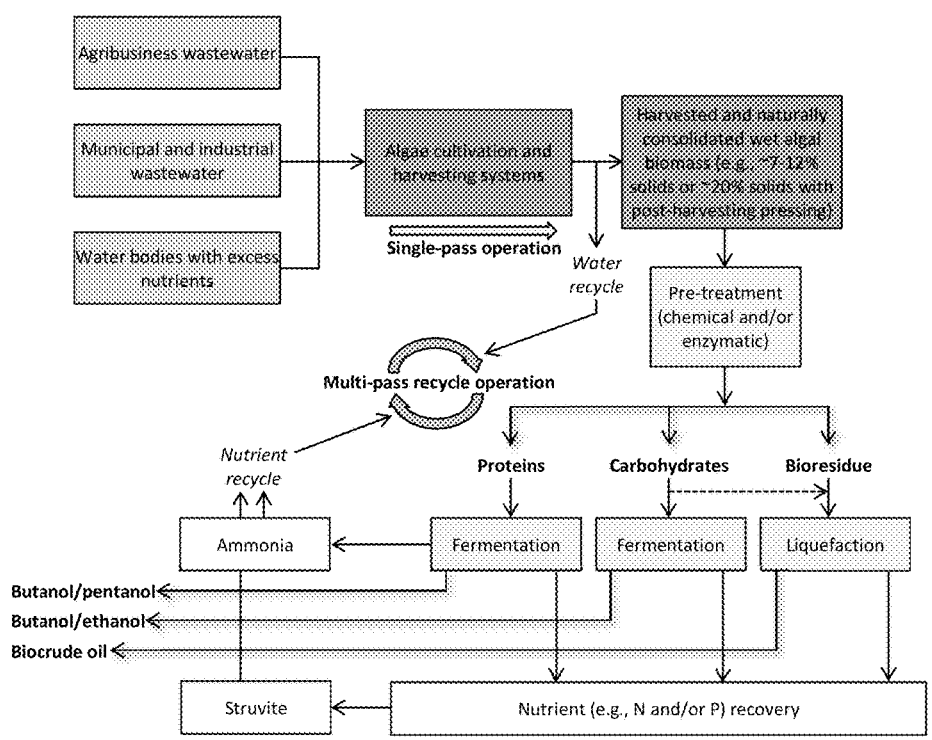
FIG. 3A-3B shows exemplary process flow diagrams for processing of algal biomass from diverse sources. Provided are (A) an exemplary process flow diagram showing single-pass and multi-pass recycle operations; and (B) an exemplary process flow diagram showing various process options.

FIG. 3A shows an exemplary process for converting algal biomass from various sources, including wastewater (e.g., agribusiness wastewater, municipal wastewater, and/or industrial wastewater), algae cultures (e.g., algae polycultures or algae monocultures), and/or water bodies with excess nutrients. Cultivation and harvesting systems can be employed to harvest algal biomass (e.g., a wet algal biomass), which can include naturally consolidated algal biomass or post-harvested, pressed algal biomass. The biomass can be pre-treated to provide biocomponents, such as proteins, carbohydrates, and a bioresidue including lipids. These biocomponents, in turn, can be fermented or liquefied.

Any fractions obtained from these biocomponents can be processed to recovery nutrients (e.g., N and/or P) in any useful form, such as a protonated form (e.g., ammonia for capturing N), an oxide form (e.g., phosphate for capturing P), a salt form, and/or a mineral (e.g., struvite for capturing N and P). The resulting biofuels and intermediates can include an alcohol (e.g., butanol, pentanol, and/or ethanol) and a biocrude oil. In addition, present petrolatum refinery operations can be employed to upgrade biocrude oil into biofuels and/or biogas.

Figure 3B:
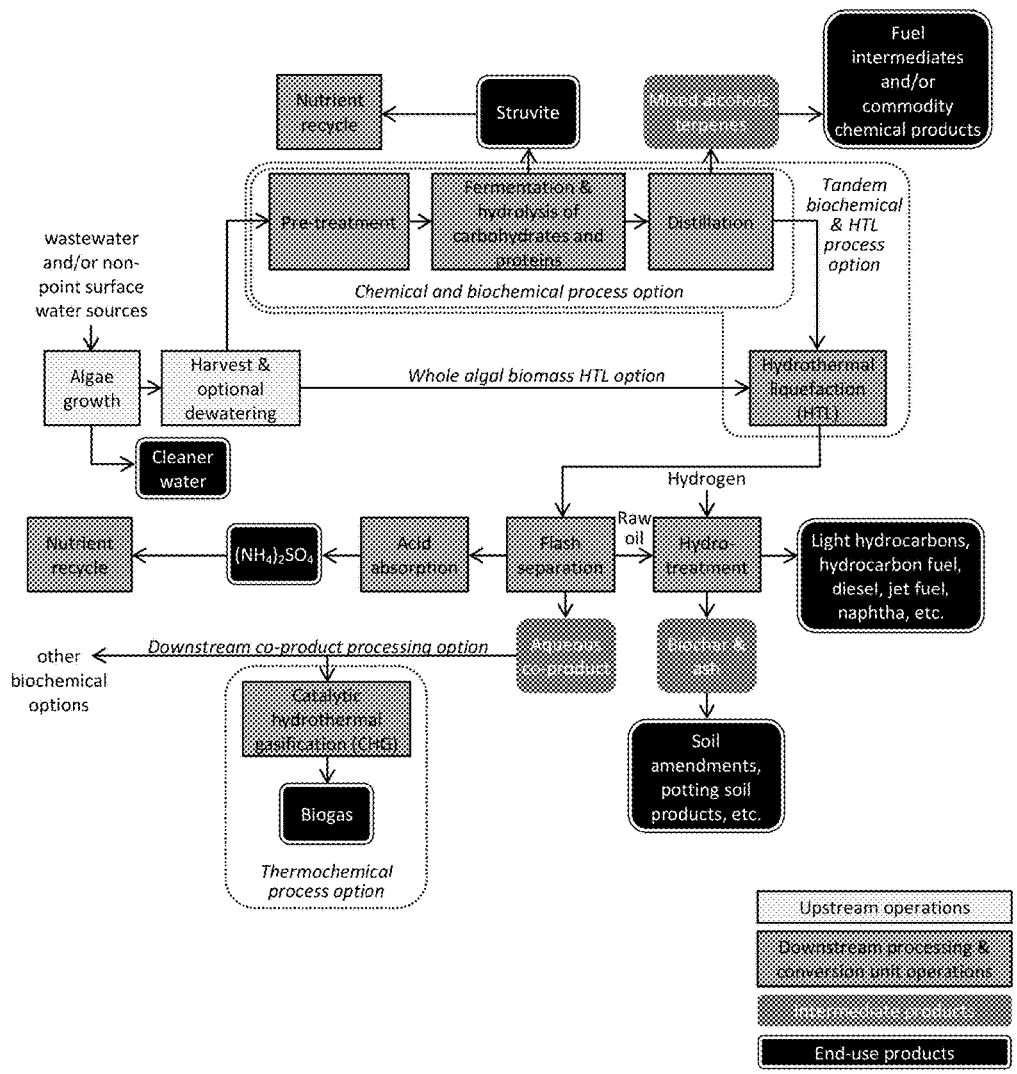

Furthermore, the process can include any combination of various options. Exemplary options include chemical and biochemical processes (e.g., to expose biocomponents within the algal biomass), thermal conversion processes (e.g., hydrothermal liquefaction (HTL), pyrolysis, gasification, combustion, and/or catalytic hydrothermal gasification (CHG) processes, such as to convert biocrude oil or aqueous co-products into useful fuels or intermediates), whole algal biomass processes (e.g., HTL of whole algal biomass), a thermochemical option (e.g., HTL or CHG processes), downstream co-product processing, and tandem processes (e.g., combining two or more of any of the processes or steps herein, such as tandem biochemical and HTL processes). FIG. 3B shows an exemplary process employing various processing options to obtain useful intermediate products and end-use products.

Algae Growth

Algae can be grown in any useful manner. For instance, the algae can be provided as a monoculture or as a polyculture (e.g., a polyculture turf biomass or benthic algal polyculture turf) grown in a pond, a bioreactor, a field plate, a tank reactor, etc.

The algae can be derived from or grown within any source, including wastewater (e.g., agribusiness, municipal, and/or industrial wastewater), as well as water bodies with excess nutrients. Biomass from high productivity polyculture sources, such as those used for waste water treatment, commonly contain 20-50% protein, 20-40% carbohydrates, 5-20% lipids, and up to 50% ash. As described herein, we have therefore investigated the potential to maximize the yield of drop-in fuels from the total constituents of the biomass using a combination of fermentation and hydrothermal liquefaction (HTL) to produce mixed alcohols (e.g., mixed C2-C8 alcohols) and low nitrogen algal biocrude oil. The benefit of biochemical conversion preceding the hydrothermal liquefaction is two-fold: (1) higher conversion efficiency to liquid fuels and chemicals, and (2) nitrogen reduction from biomass, which is a critical for HTL that would otherwise incorporate nitrogen into the final product (e.g., >5 N % in typical HTL algae crude oil). High nitrogen content bio-oils are not acceptable for processing with refineries.

The algae can include any useful organism, such as chlorophyta, diatoms, plankton, protists, and/or cyanobacteria. For instance, algae can include one or more photosynthetic organisms, including one or more microalgae, macroalgae, diatoms, green algae, yellow algae, phytoplankton, haptophytes, and/or cyanobacteria. Exemplary algae include *Achnanthes, Ankistrodesmus* (e.g., *A. falcatus* or *A. fusiformis*), *Aphanizomenon, Arthrospira* (e.g., *A. maxima*), *Bacillariophyceae, Botryococcus* (e.g., *B. braunii*), *Chlamydocapsa* (e.g., *C. bacillus*), *Chlamydomonas* (e.g., *C. perigranulata* or *C. reinhardtii*), *Chlorella* (e.g., *C. marina, C. vulgaris, C. sorokiniana, C. minutissima,* or *C. pyrenoidosa*), *Chlorococcum* (e.g., *C. infusionum, C. littorale,* or *C. humicola*), *Chlorogloeopsis* (e.g., *C. fritschii*), *Chlorophyceae, Chrysophyceae, Cyanophyceae, Dunaliella* (e.g., *D. bardawil, D. bioculata, D. primolecta, D. tertiolecta,* or *D. salina*), *Ellipsoidion, Isochrysis, Kirchneriella* (e.g., *K. lunaris*), *Nannochloropsis* (e.g., *N. salina* or *N. oculata*), *Neochloris* (e.g., *N. oleoabundans*), *Nitzschia, Phaeodactylum* (e.g., *P. tricornutum*), *Porphyridium* (e.g., *P. purpureum*), *Pyrmnesium* (e.g., *P. parvum*), *Scenedesmus* (e.g., *S. obliquus, S. quadricauda,* or *S. dimorphus*), *Schizochytrium, Skeletonema* (e.g., *S. costatum*), *Spirogyra, Spirulina* (e.g., *S. maxima* or *S. platensis*), *Synechococcus* (e.g., *S. elongatus*), and/or *Tetraselmis* (e.g., *T. maculata* or *T. suecica*). Additional algae species and organisms are described in Schneider R C S et al., "Potential production of biofuel from microalgae biomass produced in wastewater," in *Biodiesel—Feedstocks, Production and Applications*, Prof. Zhen Fang (ed.), InTech, 2012, 22 pp., which is incorporated herein by reference in its entirety.

Algae Harvest

The algae can be harvested in any useful manner. For instance, open field farms can be employed to grow algae, and mechanical harvesters can be deployed within the open field to collect the wet algal biomass. Other harvesting techniques can be employed, such as centrifugation, filtration, flocculation, fractionation, sedimentation, and/or ultrasonic separation. Dry or wet algal biomass can be employed within the conversion process, e.g., any described herein. Optionally, post-harvest consolidating and pressing can be employed to maximize the solid percentage in the algal biomass.

Pre-Treatment of the Algal Biomass

Pre-treatment can be used to convert constituents within the biomass into various biocomponents (e.g., proteins, carbohydrates, fatty acids, and/or lipids). Such biocomponents can be pre-treated to obtain more solubilized or hydrolyzed constituents, such as amino acids or sugars (e.g., glucose). For instance, carbohydrates within the biomass can be pre-treated and, thereby, be converted into a sugar and/or an alcohol, such as glucose, fucose, galactose, xylose, mannose, mannitol, ethanol, butanol, and/or pentanol. In another instance, proteins within the biomass can be treated and, thereby, hydrolyzed and converted into amino acids. Such amino acids, in turn, can be fermented to produce one or more mixed alcohols and amines. In addition, one or more extraction techniques can be applied to separate the protein/carbohydrate fraction from other constituents. Such extraction techniques can include, e.g., use of one or more ionic liquids to selectively extract a particular fraction.

Pre-treatment can include the use of one or more acids, bases, oxidizers, reducers, and/or enzymes. Exemplary pre-treatment conditions include strong and/or dilute acid hydrolysis (e.g., with $H_2SO_4$ and/or HCl), base hydrolysis or neutralization (e.g., with NaOH), heat treatment, sonication, and/or enzyme degradation (e.g., with one or more proteases, such as endoproteases, exoproteases, serine proteases (e.g., subtilisin, also known as alcalase), aminopeptidases, carboxypeptidases, endoglucanases, cellobiohydrolases, glycoside hydrolases (e.g., lysozyme), endoglucanases, glucanases, endoxyalanases, pectinases, sulfatases (e.g., arylsulfatases), as well as mixtures thereof, such that available as commercially available Pronase®, a mixture of proteolytic enzymes that are produced in the culture supernatant of *Streptomyces griseus* K-1).

Figure 4:
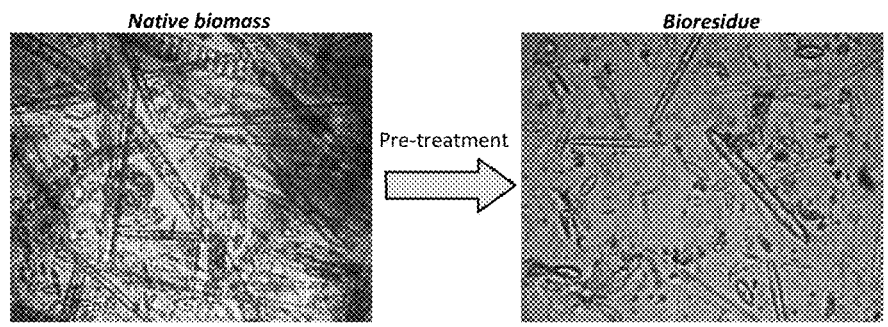
FIG. 4 shows microphotographs of an algal biomass sample before and after pre-treatment.
Figure 5A:
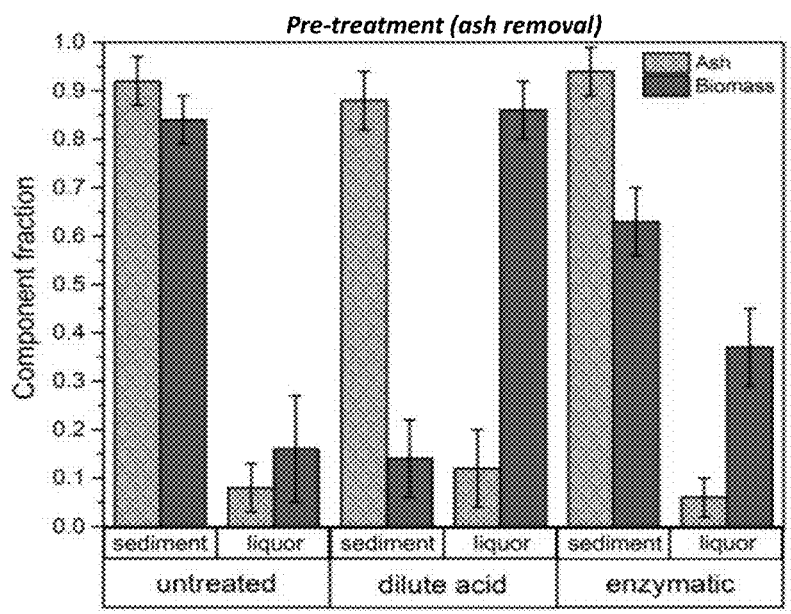
FIG. 5A-5C shows the effect of various pre-treatment conditions on algal biomass. Such pre-treatment conditions include use of dilute acid and/or enzymes. Provided are (A) the extent of ash removal from pre-treated algal biomass; (B) the extent of solubilization and hydrolysis of carbohydrate and protein fractions; and (C) an amino acid profile of the protein fraction after pre-treatment.
Figure 5B:
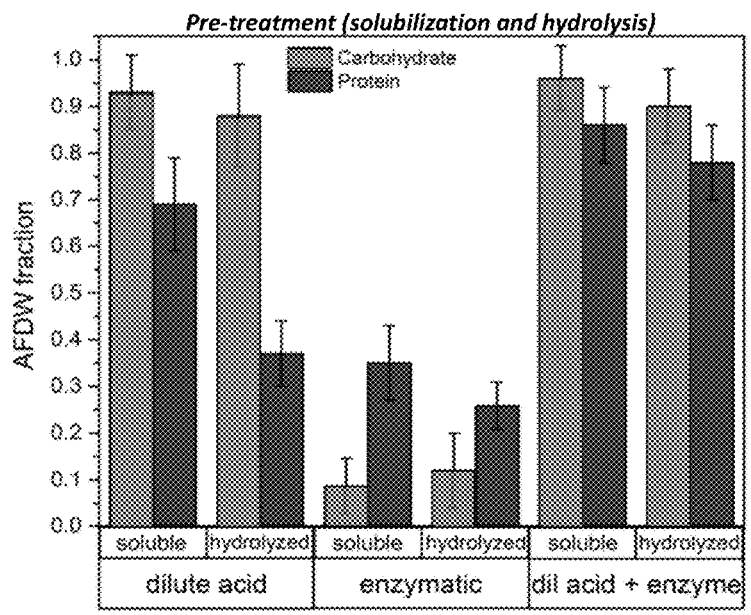

FIG. 4 shows an algal biomass sample prior to and after pre-treatment, showing degraded bioresidue that is ready for further processing. In some embodiments, a pre-treatment condition includes use of a dilute acid pre-treatment (e.g., use of 2-4% $H_2SO_4$) followed by enzymatic proteolysis that is generally applicable to benthic and microalgal biomass for sedimenting ash (FIG. 5A) and solubilizing and hydrolyzing the carbohydrate and protein fractions of the harvest algae (FIG. 5B).

Fermentation, Including Consolidated Bioprocessing

Fermentation conditions generally include the use of one or more organisms to convert starting reactants (e.g., biocomponents, such as carbohydrates, proteins, sugars, amino acids, etc.) into alcohol and other co-products. Such conditions release mixed alcohols and nitrogen, as proteins contain about 90% of the nitrogen in algal biomass. In this manner, fermentation provides not only useful biofuels and intermediates (e.g., alcohols) but also reduces nitrogen-content in biocrude oil, which is beneficial. Furthermore, release nitrogen can be recovered and recycled.

For fermentation, any useful organisms can be employed, such as one or more bacteria (e.g., *Escherichia*, such as *E. coli*; *Zymobacter*, such as *Z. palmae*; or *Zymomonas*, such as *Z. mobilis*), including mutant forms thereof, including those that deaminate protein hydrolysates (e.g., into ketoacids, tricarboxylic acid cycle intermediates, etc.), that convert proteins to alcohols (e.g., to C4 or C5 alcohols), and/or that lack one or more quorum-sensing genes (e.g., genes luxS or lsrA), such as those described in Huo Y X et al., "Conversion of proteins into biofuels by engineering nitrogen flux," *Nat. Biotechnol.* 2011; 29(4):346-51, which is incorporated herein by reference in its entirety; yeast (e.g., *Saccharomyces*, such as *S. cerevisiae* and *S. uvarum*); and fungi (e.g., *Aspergillus*, such as *A. niger, A. terreus*, and *A. fumigatus*).

Two or more different organisms can be employed for tandem processing of the biocomponents. For example, for conversion of the hydrolyzed carbohydrates and proteins to mixed alcohols, serial fermentations employ *Zymomonas* sp. and *E. coli*, respectively. Since proteins contain ~90% of the nitrogen of algal biomass, protein fermentation to mixed alcohols and ammonium provides a mechanism for reducing the nitrogen content of fuel products. Our initial studies indicate conversion of the carbohydrate fraction and protein fraction at ~90% and ~75% of theoretical yield, respectively. Furthermore, high value co-products, including butanediol isomers, acetoin, isoprenoids, and acetal have also been detected following protein fermentation.

Figure 6A:
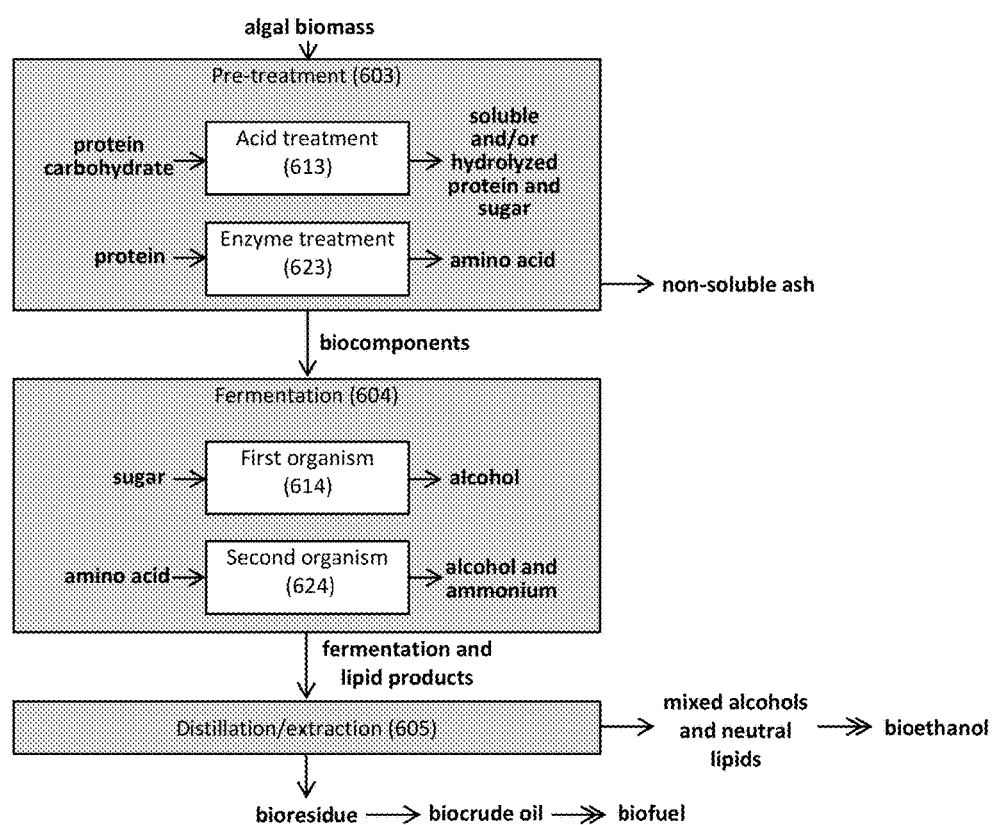
FIG. 6A-6B shows exemplary processes with various sub-steps. Provided are (A) an exemplary process including sub-steps for the pre-treatment 603 and fermentation 604 steps; and (B) an exemplary process including sub-steps for the pre-treatment 6003 and fermentation 6004 steps.

FIG. 6A shows a portion of an exemplary process including a pre-treatment step 603, a fermentation step 604, and a distillation/extraction step 605. Each of these steps, in turn, can include one or more other sub-steps. For instance, pre-treatment 603 can include acid treatment 613 in order to degrade proteins and carbohydrates into soluble and/or hydrolyzed protein and sugar; as well as enzyme treatment 623 in order to degrade proteins into amino acids. Each of these components (e.g., proteins, carbohydrates, sugars, amino acids, etc.) obtained from the pre-treatment step is considered a biocomponent. In some instances, pre-treatment 603 results in solubilization of useful biocomponents, as well as sedimentation or separation of non-soluble ash.

In another instance, fermentation can include use of one or more organisms configured to facilitate degradation (e.g., specific or non-specific degradation) of one or more biocomponents. As can be seen, an exemplary fermentation step 604 includes use of at least two organisms, in which a first organism 614 is selected for preferential degradation of sugar into alcohol and in which a second organism 624 is selected for preferential degradation of amino acid into alcohol and an amine (e.g., $N^+R^1R^2R^3R^4$ or $NR^1R^2R^3$, in which each of $R^1$, $R^2$, $R^3$, and $R^4$ is, independently, H or an optionally substituted alkyl). The fermentation step 604 results in a mixture of fermentation and lipid products. After distillation/extraction 605, various fractions of the mixture can be separated into different components, including a first fraction including mostly lipids and lipid products (i.e., a bioresidue) and a second fraction including mixed alcohols and, optionally, neutral lipids. The first fraction can be further processed (e.g., by way of liquefaction and/or pyrolysis) to produce a biocrude oil, which can be treated to form a biofuel. The second fraction can be further purified into, e.g., bioethanol. In some embodiments, the pre-treatment and fermentation conditions herein can provide enhanced alcohol yield (see, e.g., FIG. 7A-7B), as well as enhanced amino acid and ammonium yield (FIG. 7C).

The pre-treatment, distillation/extraction, and fermentation steps can be conducted in any useful order. For instance, the fermentation step can be conducted prior to distillation/extraction, meaning that lipids, proteins, and carbohydrates, as well as derived components thereof, are present during fermentation (see, e.g., FIG. 6A).

Figure 6B:
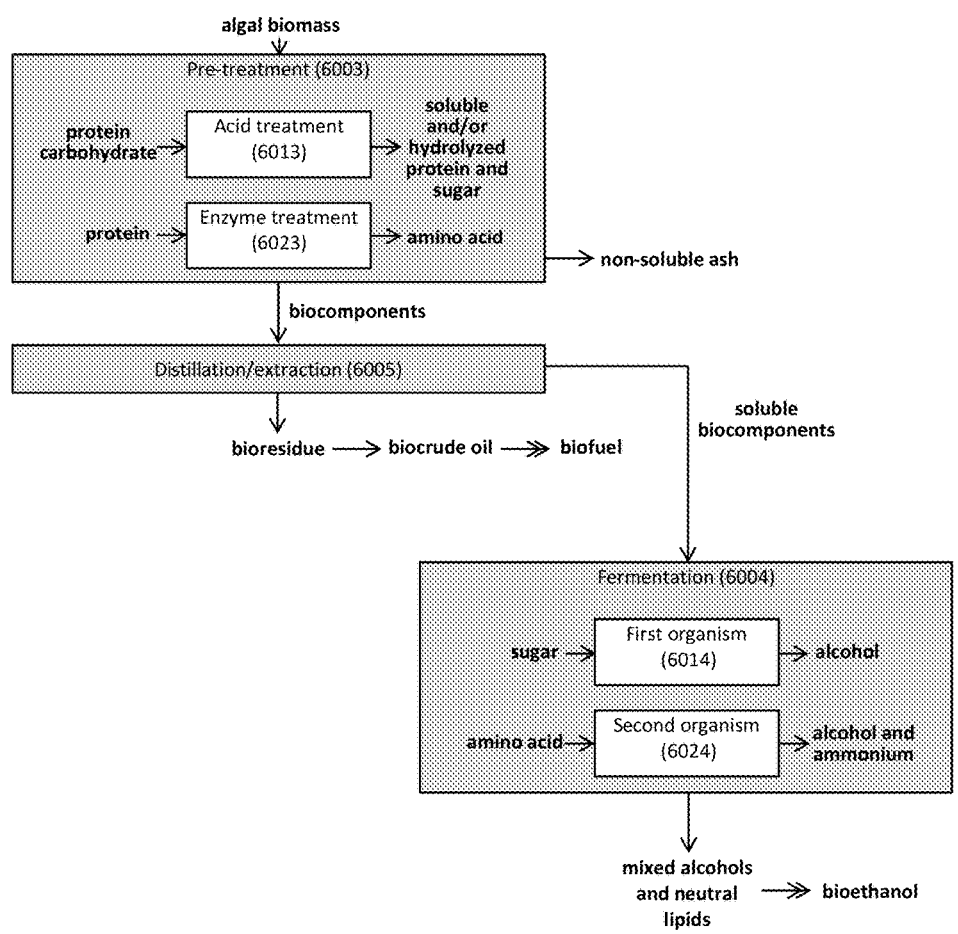

Alternatively, the distillation/extraction step can be conducted prior to fermentation, meaning that the lipid fraction will be omitted from the fermentation step. FIG. 6B shows a portion of an exemplary process including a pre-treatment step 6003, a distillation/extraction step 6005, and a fermentation step 6004. Pre-treatment 6003 can include the sub-steps of acid treatment 6013 in order to degrade proteins and carbohydrates into soluble and/or hydrolyzed protein and sugar; as well as enzyme treatment 5023 in order to degrade proteins into amino acids, thereby providing one or more biocomponents.

Next, a distillation/extraction 6005 step is conducted to provide a first fraction including mostly lipids and lipid products (i.e., a bioresidue) and a second fraction including soluble biocomponents. The first fraction can be further processed (e.g., by way of liquefaction and/or pyrolysis) to produce a biocrude oil, which can be treated to form a biofuel. The second fraction can be fermented and further purified into, e.g., bioethanol. As can be seen, an exemplary fermentation step 6004 includes use of at least two organisms, in which a first organism 6014 is selected for preferential degradation of sugar into alcohol and in which a second organism 6024 is selected for preferential degradation of amino acid into alcohol and an amine (e.g., including ammonium).

Distillation/Extraction

The alcohol fermentation products and lipids from the biomass can be captured by distillation and solvent co-extraction. Retaining the lipids through the protein fermentation has been demonstrated to increase yield by reducing product inhibition by phase segregation into lipid microparticles, which can be extracted by lipophilic solvents, such as hexane and ethyl acetate, avoiding high energy fractional distillation of the >C2 alcohol and lipid products.

Any useful distillation and extraction techniques can be employed, including flash extraction, ionic liquid extraction, etc., to isolate one or more biocrude oil, aqueous phases, aqueous co-products, nutrients, etc.

Thermal Conversion, Liquefaction or Pyrolysis

High-temperature treatment (e.g., liquefaction or pyrolysis) can be used to separate or convert particular components of the bioresidue, the biocrude oil, etc. Exemplary thermal conversion conditions include use of catalysts, use of hydrogen (e.g., in hydrotreatment), use of water (e.g., in liquefaction, including sub-critical or super-critical water), use of aerobic conditions, use of anaerobic conditions (e.g., in pyrolysis), use of high pressure (e.g., of from about 2,000 psi to about 3,000 psi), and/or use of high temperatures (e.g., of from about 200° C. to about 800° C.) to decompose the bioresidue into small molecules, which in turn can react and repolymerize to form oily compounds within a biocrude oil.

In one instance, the thermal conversion condition includes liquefaction, which is generally conducted in the presence of water (e.g., such as water that is present in a wet algal biomass). By using high temperature and/or high pressure conditions, water becomes a reactive compound that converts the bioresidue into a biocrude oil. Exemplary liquefaction conditions include a wet algal biomass (e.g., more about 70% moisture), a temperature of from about 200° C. to about 500° C., and a pressure of from about 4 to about 25 MPa.

In another instance, the thermal conversion condition includes pyrolysis, which is generally conducted in the absence of water and in anaerobic conditions. Exemplary pyrolysis conditions include a dry algal biomass (e.g., less than about 5% moisture), a temperature of from about 200° C. to about 750° C., and a pressure of from about 0.1 to about 0.5 MPa. Exemplary thermal conversion conditions are described in Ma F et al., "Biodiesel production: a review," *Bioresource Technol.* 1999; 70:1-15; Naik S N et al., "Production of first and second generation biofuels: a comprehensive review," *Renew. Sustain. Energy Rev.* 2010; 14:578-97; Raheem A et al., "Thermochemical conversion of microalgal biomass for biofuel production," *Renew. Sustain. Energy Rev.* 2015; 49:990-9; Ringer M et al., "Large-scale pyrolysis oil production: a technology assessment and economic analysis," *National Renewable Energy Laboratory Technical Report NREL/TP*-510-37779, November 2006, 93 pp.; and Schneider R C S et al., "Potential production of biofuel from microalgae biomass produced in wastewater," in *Biodiesel—Feedstocks, Production and Applications*, Prof. Zhen Fang (ed.), InTech, 2012, 22 pp., each of which is incorporated herein by reference in its entirety.

In non-limiting embodiments, we have demonstrated ~40% biocrude yield from algae biomass using non-catalytic HTL. Furthermore, the aqueous phase of HTL contained high quantities of remineralized phosphate for subsequent nutrient recapture, potentially as struvite ($NH_4MgPO_4$) fertilizer. Furthermore, biochar and diatomaceous earth produced in the process can be captured for agricultural applications. In one non-limiting embodiment, the biocrude oil is a complex mixture including one or more of the following: aliphatic alcohols, aldehydes, benzenoids, fatty acids, furanoids, pyranoids, and/or hydrocarbons (e.g., low and/or high molecular mass hydrocarbons).

Any of the liquefaction steps herein can be replaced by any other thermal conversion step (e.g., pyrolysis for use with a dry algal biomass) in which high temperature conditions are employed to thermally degrade a bioresidue.

Figure 8A:
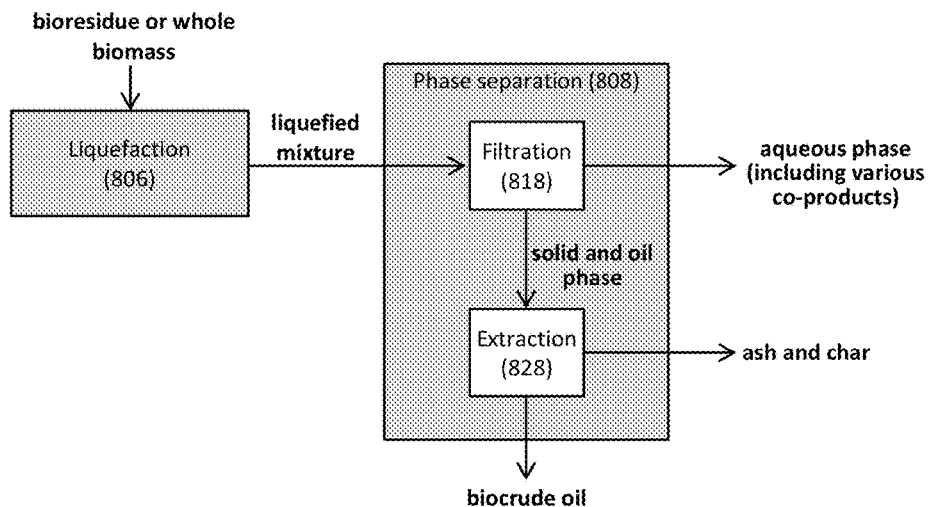
FIG. 8A-8D shows the effect of an exemplary liquefaction process on the whole biomass or on the pre-treated, fermented biomass (bioresidue). Provided are (A) an exemplary process with liquefaction 806 and phase separation 808 steps; (B) a graph showing loss of sample weight upon liquefaction within a temperature range of from about 100° C. to 800° C.; (C) fractions of a liquefied whole biomass (a wet biomass with 10% solids) producing a biocrude having about 4.5% nitrogen content and about 44% yield; and (D) fractions of a liquefied bioresidue producing a biocrude having about 0.89% nitrogen content and about 22% yield.

FIG. 8A shows a portion of an exemplary process including a liquefaction step 806 to produce a liquefied mixture and a phase separation step 808 to separate components within that mixture. Phase separation 808 can include the sub-steps of filtration 818 in order to separate solid, oil, and aqueous phases; as well as solvent extraction 828 in order to obtain the biocrude oil.

Hydrotreatment

Hydrotreatment is generally used to convert compositions into useful intermediate products or end-use products. Such hydrotreatment generally includes use of high temperatures to institute any useful chemical change, e.g., to break apart triglycerides; to form low molecular weight carbon species, such as optionally substituted alkanes, cycloalkanes, or aryls; to saturate carbon chains with hydrogen; to denitrogenate species; and/or to deoxygenate species to form alkanes, such as n-alkanes. For instance, hydrotreatment can be used to upgrade biocrude oil into biofuels, biochar, or ash; as well as to convert aqueous co-products into biogas. Biocrude oil produced from the post-fermentation residuals by HTL is indicated to have ~50% reduction in nitrogen (primary and secondary amines), thus making it acceptable for hydrotreatment using the existing petrochemical infrastructure.

Hydrotreatment can include isomerization, hydrocracking, distillation, hydrodeoxygenation, catalytic processing (e.g., such as use of one or more catalysts to remove nitrogen, oxygen, and/or sulfur from the biocrude oil under any useful condition, such as a pressure of from about 5 MPa to about 15 MPa and a temperature of from about 200° C. to about 450° C.), liquefaction (e.g., such as hydrothermal liquefaction (HTL) or catalytic liquefaction of a biocrude oil into a biofuel or a biofuel intermediate by use of an operating temperature of from about 100° C. to about 500° C.), transesterification (e.g., treatment of biocrude oil with an alcohol and an optional catalyst to produce methyl ester biodiesel), and/or catalytic hydrothermal gasification (CHG) (e.g., of an aqueous co-product into biogas).

The hydrotreatment process can employ any useful catalyst (e.g., a metal catalyst, such a copper-based catalyst (e.g., CuCr, CuO), a nickel-based catalyst (e.g., NiMo), a ruthenium-based catalyst, a palladium-based catalyst (e.g., Pd/C), a platinum-based catalyst, a rhenium-based catalyst, or a cobalt-based catalyst (e.g., CoMo)) in the presence of any carrier (e.g., a zeolite, an alumina, etc.); any useful reagent, such as hydrogen (e.g., $H_2$) or water (e.g., supercritical water); any useful pressure, e.g., such as from about 3 MPa to about 30 MPa (e.g., from about 5 MPa to about 20 MPa); and/or any useful temperature, e.g., such as from about 100° C. to about 500° C. (e.g., from about 250° C. to about 350° C.). Further exemplary hydrotreatment conditions are described in Ma F et al., "Biodiesel production: a review," *Bioresource Technol.* 1999; 70:1-15; Tran N H et al., "Catalytic upgrading of biorefinery oil from micro-algae," *Fuels* 2010; 89:265-74; and Wildschut J et al., "Catalyst studies on the hydrotreatment of fast pyrolysis oil," *Appl. Catalysis B* 2010; 99:298-306, each of which is incorporated herein by reference in its entirety.

Exemplary biofuels formed by hydrotreatment include naphtha, biodiesel (e.g., including one or more unsaturated fatty acids or fatty acid esters, such as of from about 10% to about 35% of a long chain fatty acid having a $C_{13}$-$C_{21}$ tail, such as a palmitic fatty acid ($C_{16}$ tail), linoleic fatty acid ($C_{18}$ tail), oleic fatty acid ($C_{18}$ tail), and/or stearic fatty acid ($C_{18}$ tail)), green diesel, renewable aviation fuel, hydrocarbons (e.g., light hydrocarbons), alcohol (e.g., ethanol; propanol, such as 1-propanol; butanol, such as n-butanol, isobutanol, 2-butanol, 3-butanol, 2-methyl-1-butanol, 3-methyl-1-butanol, etc.), and/or a biogas (e.g., hydrogen or methane). Other products formed by hydrotreatment include solid residuals (e.g., biochar and ash), aqueous co-products (e.g., ketoacids, amines, nutrients, etc.), as well as other useful co-products (e.g., animal feed, fertilizer, glycerine, biopolymers, etc.).

Phase Separation

Phase separation steps can be employed to separate components of a liquefied mixture, fermentation broth, aqueous fraction, a non-aqueous fraction, alcohol fraction, etc. Such steps include any that separate liquid from solid phases, as well as separate two or more phases that can be differentiated based on solubility, miscibility, etc. (e.g., as those present in non-aqueous phases, aqueous phases, lipophilic phases, etc.) in any useful solvent (e.g., an organic solvent, an aqueous solvent, water, buffer, etc.). Phase separation techniques include flash separation (e.g., separation of liquefied mixture into biocrude oil, solid residuals, aqueous phase, and/or aqueous co-products), acid absorption (e.g., absorption of acid in a matrix to provide recovered nutrients and water for recycled use), filtration, distillation, solvent extraction, ion liquid extraction, etc. The resultant products and co-products can include one or more intermediate products that can optionally be processed to form useful end-use products (e.g., see FIG. 3B, in which intermediate products of ash and biochar are further processed to provide solid residuals for soil amendments and potting soil products).

Nutrient and/or Water Recovery

From any co-products produced in the methods herein, one or more nutrients, as well as water, can be recovered for potential recycled use. The conversion process herein releases nitrogen that is captured within the algal biomass (e.g., as amino groups in proteins), and nitrogen is a limited resource that can be recycled with the processes described herein. This conversion process also releases phosphorous, which can also be captured, recovered, and recycled. In particular, nitrogen (N) and phosphorous (P) can be recovered as ammonium and phosphate nutrients, which can be optionally remineralized as a salt (e.g., a struvite, an ammonium sulfate, etc.) in any useful form, such as in a solid form.

Success in implementation of the process describe here can be extrapolated to algae culture in the southern stretch of the Mississippi River and Delta, where N/P nutrient removal is anticipated to combat the negative environmental and economic effects of the Gulf of Mexico "Dead Zone." Based on capture of 10% of the total quantity of nitrogen discharged from the Mississippi River (1.567M tons), we calculate that 783.5 million gallons of biofuel could be produced on 156,700 acres of algal cultures. The land area requirement for this endeavor corresponds to less than 1% of the approximate surface area of Mississippi Delta.

EXAMPLES

Example 1: Algal Turf to Fuel-Production of Biofuels from Chemical, Biochemical, and Thermochemical Processing and Conversion of Benthic Polyculture Biomass Produced by Algal Turf Cultivation Turf algal biomass for fuels offers significant benefits over raceway monoculture systems. For instance, turf algal biomass generally includes a polyculture of different algae, thereby increasing the resilience of the biomass from crashes due to environment stresses and promoting robust algae production. In addition, growth is maximized, while costly addition of nutrients and $CO_2$ is minimized. Finally, expensive harvesting and dewatering of the biomass can be minimized or even avoided. For instance, simple mechanical harvesting can provide a biomass with 8% to more than 15% solids content within the wet biomass.

In one instance, the purpose of this invention is high efficiency conversion of wet (e.g., 5-10% solids) algae biomass into fuel intermediates that are suitable for downstream refining using the existing petrochemical infrastructure. Our integrated process can accommodate a wide variety of biomass compositions, as well as avoid the high energy costs associated with extensive biomass dewatering. In addition, the process herein facilitates removal of nitrogen and ash from the material. Specifically, in some non-limiting examples, the process combines wet pre-treatment to solubilize and hydrolyze the carbohydrate and protein fractions followed by fermentation, lipid and alcohol co-extraction, nitrogen/phosphorous (N/P) nutrient capture, and hydrothermal liquefaction of the residuals.

Accordingly, in one instance, we propose an integrated biochemical and thermochemical process to achieve increased yield of high purity algae biofuels using the approach illustrated in FIG. 1B. The conversion process 20 includes several features, including pre-treatment 23 of the biomass to provide at least three different biocomponents: proteins, carbohydrates, and the remaining bioresidue including one or more algae-derived lipids. The lipid fraction is liquefied 26 and hydrotreated 27 to form high-energy bio-oils and biofuels, whereas the protein and carbohydrate fraction(s) are fermented 24 and distilled 25 to form alcohols, hydrocarbons, and other bioproduct feedstock. In addition, any aqueous fractions obtained from the biomass can be further processed 28 to recover any water-soluble nutrients, e.g., nitrogen in the form of ammonium or phosphorous in the form of phosphate, as well as to recover any water for return to the algal culture. In particular, this streamlined, consolidated process offers a way to use all components of the algal culture to maximize product yield, minimize waste, and/or provide a high purity, low nitrogen biocrude oil (e.g., a nitrogen content of less than 1%).

Another exemplary process for treating a polyculture biomass is described in FIG. 3A. As can be seen, this process includes pre-treatment to expose biocomponents (FIG. 4); biochemical conversion of the proteins and carbohydrates; as well as thermochemical conversion, by way of hydrothermal liquefaction (HTL), of the bioresidue (including one or more lipids) into biocrude oil (see, e.g., FIG. 6A-6B). Additional details are described in the following examples.

Example 2: Pre-Treatment and Ash Removal from Algal Biomass

The basic chemical profile of microalgae—roughly equal ratios of lipids, proteins, and polysaccharides (carbohydrates)—requires that the value of the biomass be optimized by making use of all of the algal biocomponents. These biocomponents can become renewable sources for biofuels, bioethanol, and other by-products. One hurdle lies in converting the cellular material into a form suitable for fuels production. This conversion requires rupturing the algal cell walls for releasing the lipids, and breaking down the protein and polysaccharide fractions to generate a viable medium for fermentative conversion.

Algal biomass can be treated to expose its biocomponents. For instance, such treatments can include pre-treatment (e.g., with dilute acid hydrolysis, strong acid hydrolysis, and/or enzymatic hydrolysis) and fermentation (e.g., with one or more bacteria, including mutant forms thereof). Pre-treatment generally led to the formation of insoluble bioresidue and soluble biocomponents (e.g., soluble protein and/or carbohydrate biocomponents). In addition, depending on the pre-treatment conditions, soluble biocomponents can be further hydrolyzed or degraded. For instance, carbohydrates can be degraded into sugars, and/or proteins can be degraded into amino acids.

Pre-treatment also led to the separation of ash from the biocomponents. Thus, this pre-treatment step is effective for ash removal (FIG. 5A).

Various pre-treatment conditions were tested. Dilute acid hydrolysis was employed to convert the majority (about 90%) of carbohydrates to glucose (FIG. 5B, left). Under these hydrolysis conditions, proteins were only about 40% hydrolyzed to amino acids (FIG. 5B, left). There was a strong preference for amino acids for conversion to mixed alcohols. Enzymatic pre-treatment led to protein hydrolysis (FIG. 5B, center). By combining dilute acid hydrolysis with enzyme treatment (Pronase®), the majority fraction for both carbohydrates and proteins were soluble and hydrolyzed (FIG. 5B, right).

Figure 5C:
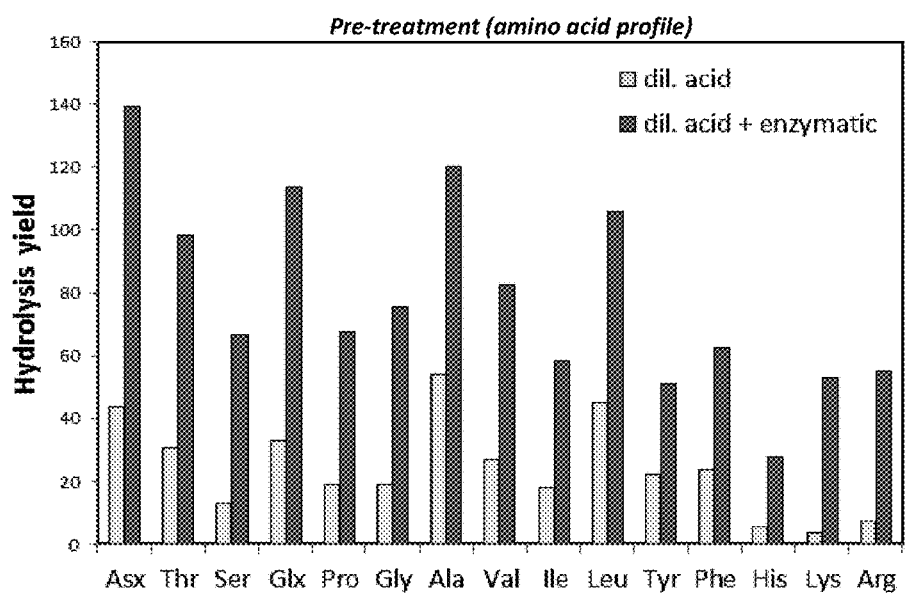

High quantities of non-natural amino acids were also detected in pre-treated residual solids, including γ-aminobutyric acid, β-aminoisobutyric acid, and β-alanine (FIG. 5C). Such non-natural amino acids can be further purified for use as chemical building blocks (e.g., for pharmaceutical use). In particular, dilute acid was effective for solubilizing the protein and carbohydrate fractions and for hydrolyzing carbohydrates, but additional enzymatic treatment was necessary for protein solubilization and hydrolysis.

Example 3: Microaerobic Fermentation of Algal Biomass Residuals for Mixed Alcohol Production Algal biomass is composed of roughly equal fractions of lipids, carbohydrates, and proteins. The protein content is significantly higher than most terrestrial and multicellular organisms, and protein compositional variation is low. The conversion of carbohydrates and proteins to alcohols shows promise for increasing biofuel yields with significant potential for side benefits, including boosting octane and reducing particulate emissions by way of fuel blending. In addition, the conversion of proteins to amino acids can lead to new avenues for producing biofuels, industrial chemicals, and pharmaceuticals.

After pre-treatment, fermentation with bacteria was employed to further process sugars, proteins, amino acids, and carbohydrates into simpler compounds, such as alcohols and amino-compounds, such as ammonium. Fermentation conditions included use of metabolically engineered *E. coli* strains, such as those described in Huo Y X et al., "Conversion of proteins into biofuels by engineering nitrogen flux," *Nat. Biotechnol.* 2011; 29(4):346-51, which is incorporated herein by reference in its entirety. Such strains can be modified to have alcohol tolerance, reduction of quorum-sensing, and assimilation of nitrogenous carbon sources.

Fermentation yields were measured for pre-treated *Chlorella* microalgae (FIG. 7A) and *Scenedesmus* microalgae (FIG. 7B). Most fermentation processes were complete at 6-21 hours, and controlled fermentation was achieved (e.g., more than about 90% conversion of sugars into ethanol).

Pre-treatment and fermentation conditions can be included in any useful manner. In one instance, a five-step process included dilute acid pre-treatment; ethanolic fermentation; distillation; enzymatic digestion of proteins; and microaerobic fermentation (e.g., at 37° C. for 96-120 hours). The accumulation of alcohols proceeded in distinct temporal phases, where formation of different alcohol compounds included initial formation of isobutanol, followed by n-methyl-butanol, and then phenylethanol with n-butanol (FIG. 7C). The accumulation of ammonium increased as amino acids were depleted and was stoichiometric with alcohol production, suggesting that amino acid break-down products included alcohol and ammonium.

There was evidence of metabolic inhibition by some chemical components of the algal biomass slurry (e.g., inhibitory components can include accumulation of ammonium, alcohols, phospholipids, etc.). Optimization steps can include thermal trapping of alcohol during fermentation, removal of such inhibitory chemical components, lipid extraction to provide higher alcohol yields, ionic liquid pre-treatment, as well as precipitation of accumulated ammonium as phosphate mineral salts.

Consolidation of lipid and alcohol recovery unexpectedly led to enhanced fermentation. During pre-treatment, lipid microparticles are generally released from the algae. Retaining these lipids and lipid particles in the protein fermentation broth appeared to reduce alcohol toxicity to the organisms employed for fermentation. In addition, microparticle size distribution shifted in the presence of mixed alcohols, leading to co-extraction of neutral lipids and mixed alcohols. The co-extracted phase can optionally be further processed to separate the mixed alcohols and lipid phases (e.g., by using a lipophilic solvent, such as hexane). Then, the mixed alcohols can be further purified into, e.g., bioethanol; and the neutral lipids can be further recovered and treated by way of liquefaction to increase production yield of the biocrude oil.

Aeration during fermentation was adjusted in order to optimize fermentation conditions. In bench-scale (1 L) fermentation experiments, we discovered that oxygen ($O_2$) was beneficial for an initial period of about 12-14 hours at the beginning of fermentation. After this initial period, oxygen was purged and replaced with nitrogen ($N_2$). The residence time was decreased from 96 hours to 48 hours by employing an initial aerobic condition followed by incubation under anaerobic conditions. These conditions can be further optimized (e.g., by controlling the initial aerobic period or the biomass loading) to obtain beneficial residence times and conversion yield.

Any processes herein can be consolidated to maximize efficiency, while maintaining production of bioethanol, biocrude oil, etc. For instance, sugars and protein can be co-fermented by employing a mixture of organisms (e.g., yeast, bacteria, etc.) in which at least one organism preferentially degrades sugars to alcohols and at least one other organism preferentially degrades proteins into amino acids, alcohols, and/or ammonium. In another instance, organisms can be modified to heterologously express proteases, which in turn will break down proteins to simpler amino acid components. In yet another instance, sugars, proteins, and lipids are fermented together.

Overall, the conditions herein allowed for optimal hydrolysis of algal biomass into mixed alcohols, which in turn can be further processed into bioethanol. Further, pre-treatment conditions resulted in the formation of an insoluble bioresidue including lipid material that can be further processed into biocrude oil, which in turn can be refined into a biofuel.

Figure 8B:
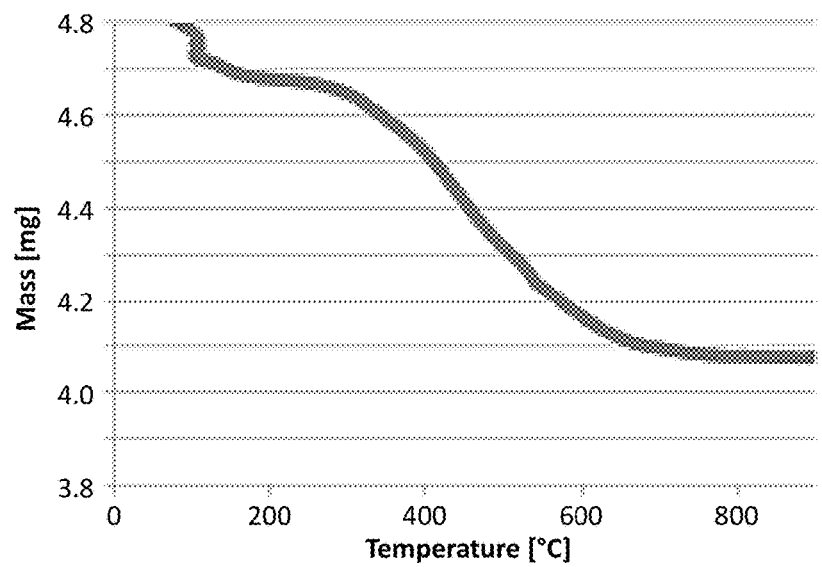

Example 4: Thermochemical Conversion of Whole Biomass or Processed Bioresidue Either the whole biomass (e.g., directly after pre-treatment) or the processed bioresidue (e.g., after pre-treatment and fermentation) can be treated with a thermochemical process to produce a biocrude oil (FIG. 8A). Using hydrothermal liquefaction (HTL), the biomass or bioresidue is exposed to high temperatures (e.g., of from about 200° C. to 800° C., FIG. 8B), which results in the formation of volatiles and chemical monomers, as well as the separation of products into various gas, solid, aqueous, and non-aqueous phases.

Figure 8C:
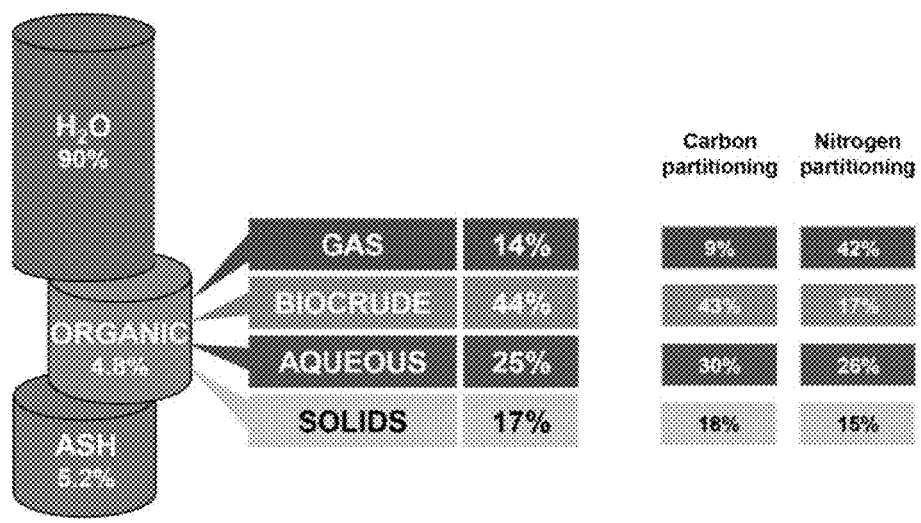

In an un-optimized HTL process, we processed both a whole biomass and a bioresidue. For a whole biomass treated with HTL, we obtained a high yield (about 44%) of biocrude oil by converting wet algal biomass with 10% solids (FIG. 8C). The nitrogen content in the biocrude oil was about 4.5%. This biocrude oil can be further processed to remove nitrogen, as needed.

Figure 8D:
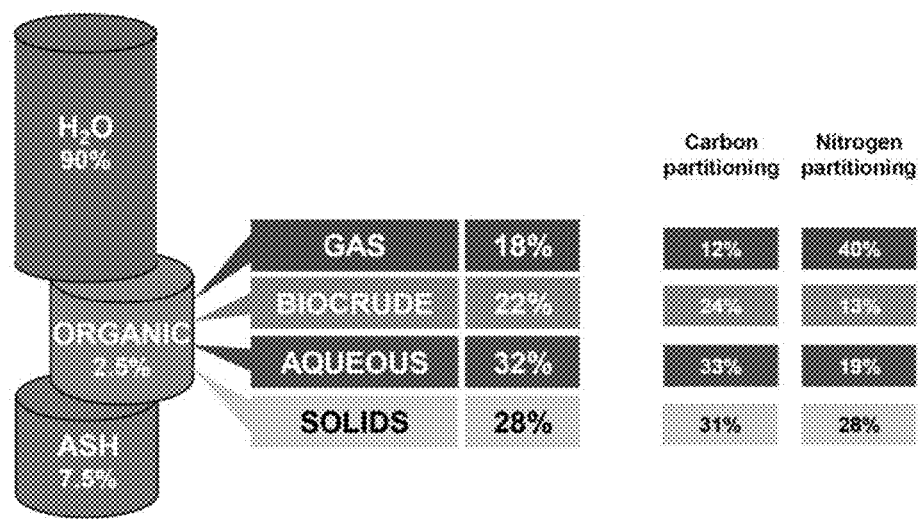

Rather than the whole biomass, algae can be pre-treated, fermented, and distilled in order to produce an organic bioresidue. In some instances, pre-treatment, fermentation, and distillation can provide a low nitrogen content bioresidue, which is beneficial as high nitrogen content cannot be tolerate in some refineries. Then, this bioresidue can be thermally treated to produce a biocrude oil. When a bioresidue was treated with HTL, we obtained a biocrude oil at a lower yield (about 22%) but with a significantly lower nitrogen content (about 0.89%) (FIG. 8D). For both the whole biomass and bioresidue, the HTL process can be optimized to increase yield (e.g., by recovering carbon-based components in the aqueous co-products and solids or by including carbohydrates with the biomass or bioresidue) and/or decrease nitrogen content (e.g., by removing nitrogen-based compounds with remineralization).

Example 5: Nutrient Recovery

The potential for nutrient recovery (e.g., recovery of ammonium and phosphate, such as by way of remineralization) can provide a way to institute multi-pass recycle operations, in which recovered nutrients can be used to supplement and propagate algae growth and cultivation. Both point sources and non-point sources of water can be treated to clean the water source, to recover excess biocomponents and nutrients, and/or to recycle nutrients for upstream algal cultivation.

Other Embodiments

All publications, patents, and patent applications, including U.S. Provisional Application Nos. 62/017,118 and 62/017,121, each filed Jun. 25, 2014, mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of converting algal biomass, the method comprising:
   a) pre-treating the algal biomass with one or more acids and/or one or more enzymes, thereby providing one or more biocomponents and releasing lipid microparticles from the algal biomass;
   b) fermenting a fermentation broth comprising the lipid microparticles and the one or more biocomponents, thereby providing an alcohol and a bioresidue;
   c) determining a shift in a microparticle size distribution of the lipid microparticles, wherein the shift indicates a presence of the alcohol from step b);
   d) separating the alcohol from the bioresidue; and
   e) liquefying and/or pyrolyzing the bioresidue, thereby providing a biocrude oil.

2. The method of claim 1, wherein the algal biomass comprises a wet algal biomass.

3. The method of claim 1, wherein the algal biomass comprises a polyculture biomass.

4. The method of claim 1, wherein the one or more biocomponents comprise one or more proteins and/or carbohydrates derived from the algal biomass.

5. The method of claim 1, wherein the biocrude oil has a low nitrogen content.

6. The method of claim 1, wherein the pre-treating step a) comprises i) treating the algal biomass with one or more acids and ii) treating with one or more enzymes, wherein the steps i) and ii) can be conducted sequentially in any order or at the same time.

7. The method of claim 1, wherein the fermenting step b) comprises exposing the one or more biocomponents to one or more organisms or mutant forms thereof.

8. The method of claim 1, wherein the fermenting step b) comprises use of an aerobic and/or an anaerobic condition.

9. The method of claim 1, further comprising, after the fermenting step b), removing one or more by-product nutrients present in a same phase as the alcohol.

10. The method of claim 1, wherein in the determining step c), the presence of the alcohol indicates the presence of mixed alcohols.

11. The method of claim 1, wherein the lipid microparticles comprise one or more triglycerides and one or more fatty acids.

12. The method of claim 1, wherein the alcohol is present in a first phase and the bioresidue is present in a second phase that is separate from the first phase.

13. The method of claim 1, wherein the separating step d) is conducted by extracting the bioresidue with one or more lipophilic solvents or solvent mixtures.

14. The method of claim 1, further comprising, after the separating step d), processing the alcohol to provide a purified bioethanol.

15. The method of claim 14, wherein the alcohol is selected from the group consisting of ethanol, propanol, butanol, and alkylated formed thereof.

16. The method of claim 1, wherein the liquefying and/or pyrolyzing step e) comprises exposing the bioresidue to a non-catalytic condition comprising a temperature of from about 200° C. to about 500° C.

17. The method of claim 16, wherein the liquefying and/or pyrolyzing step e) further provides a biochar.

18. The method of claim 17, further comprising, after the liquefying and/or pyrolyzing step e), separating the biocrude oil from the biochar.

19. The method of claim 16, wherein the liquefying and/or pyrolyzing step e) further provides an aqueous phase comprising one or more nutrients.

20. The method of claim 19, further comprising, after the liquefying and/or pyrolyzing step e), separating the biocrude oil from the aqueous phase; and capturing the one or more nutrients present in the aqueous phase.

21. The method of claim 1, further comprising, after the liquefying and/or pyrolyzing step e), upgrading the biocrude oil into one or more biofuels.

22. A method of converting algal biomass, the method comprising:
   a) pre-treating the algal biomass with one or more acids and/or one or more enzymes, thereby providing one or more biocomponents and releasing lipid microparticles from the algal biomass;
   b) fermenting a fermentation broth comprising the lipid microparticles and the one or more biocomponents, thereby providing an alcohol and a bioresidue;
   c) determining a shift in a microparticle size distribution of the lipid microparticles wherein the shift indicates a presence of the alcohol from step b);
   d) liquefying and/or pyrolyzing the bioresidue, thereby providing a biocrude oil and an aqueous phase; and
   e) capturing one or more nutrients present in the aqueous phase.

23. The method of claim 22, wherein capturing the one or more nutrients comprises recovering struvite.

24. A method of converting algal biomass, the method comprising:
   a) pre-treating the algal biomass with one or more acids and/or one or more enzymes, thereby providing a combination of an ash and one or more biocomponents and releasing lipid microparticles from the algal biomass;
   b) separating the ash from the combination;
   c) fermenting a fermentation broth comprising the lipid microparticles and the one or more biocomponents, thereby providing an alcohol and a bioresidue;
   d) determining a shift in a microparticle size distribution of the lipid microparticles, wherein the shift indicates a presence of the alcohol from step c);
   e) separating the alcohol from the bioresidue;
   f) liquefying and/or pyrolyzing the bioresidue, thereby providing a biocrude oil and an aqueous phase; and
   g) capturing one or more nutrients present in the aqueous phase.

25. The method of claim 1, wherein fermenting step b) comprises providing an initial aerobic period comprising oxygen, purging the oxygen after the initial aerobic period, and then providing an anaerobic period comprising nitrogen.

* * * * *